United States Patent [19]

Holm et al.

[11] 4,172,524

[45] Oct. 30, 1979

[54] INSPECTION SYSTEM

[75] Inventors: James P. Holm; Joe W. Clapper, both of Kalamazoo; Ronald J. Dudley, Vicksburg; Chester C. Sperry, Kalamazoo, all of Mich.

[73] Assignee: The Upjohn Company, Kalamazoo, Mich.

[21] Appl. No.: 793,527

[22] Filed: May 4, 1977

[51] Int. Cl.² ............................................. B07C 5/342
[52] U.S. Cl. .................................. 209/524; 209/698; 209/919; 209/565; 198/480; 250/223 B; 356/427; 358/81
[58] Field of Search ..................... 209/73, 74 R, 74 M, 209/111.5, 111.7 T, 74 R, 523, 524, 526, 563, 564, 565, 588, 698, 919; 250/223 B, 576; 356/197, 198, 240; 198/339, 480, 481; 358/81, 82, 106, 107

[56] References Cited

U.S. PATENT DOCUMENTS

| | | | |
|---|---|---|---|
| 2,454,412 | 11/1948 | Stoate | 250/223 B |
| 3,455,443 | 7/1969 | Wilder | 209/74 R |
| 3,480,140 | 11/1969 | Unkefer | 209/74 R X |
| 3,563,379 | 2/1971 | Stapf et al. | 209/111.7 T |
| 3,765,533 | 10/1973 | Stephens et al. | 356/197 X |
| 3,811,567 | 5/1974 | Tomita et al. | 209/73 |
| 3,849,793 | 11/1974 | Ablett | 358/107 X |

Primary Examiner—Joseph J. Rolla
Attorney, Agent, or Firm—Blanchard, Flynn, Thiel, Boutell & Tanis

[57] ABSTRACT

An inspection system for detecting excessive particulate matter in serially presented liquid filled vials. Vials are advanced by an in-feed star wheel, a rotating vial deck and an out-feed star wheel having the same number of vial locations and vial orbit speed. Along the vial deck orbit, each vial is successively clamped to a rotatable puck, spun momentarily to swirl the liquid therein, inspected for particulate content, and unclamped. Further rotating decks carry circumferentially arranged television cameras and light sources, respectively. Each camera looks radially inward, axially through an orbiting periscope and then radially outward to inspect a vial. Light from each light source passes radially inward and then axially to bottom light its vial. A separation unit enhances the camera video portion corresponding to swirling particles in the vial. A processor unit then detects particles in a window area overlying the swirling vial liquid by assessing the width along a scan line and occurrence in successive scan lines of a video disturbance and repetition of that disturbance in several successive scanning fields of the camera. A vial reject unit and a color CCTV monitor are provided. One or more separator-processor units and a monitor may be time shared by a plurality of cameras.

33 Claims, 18 Drawing Figures

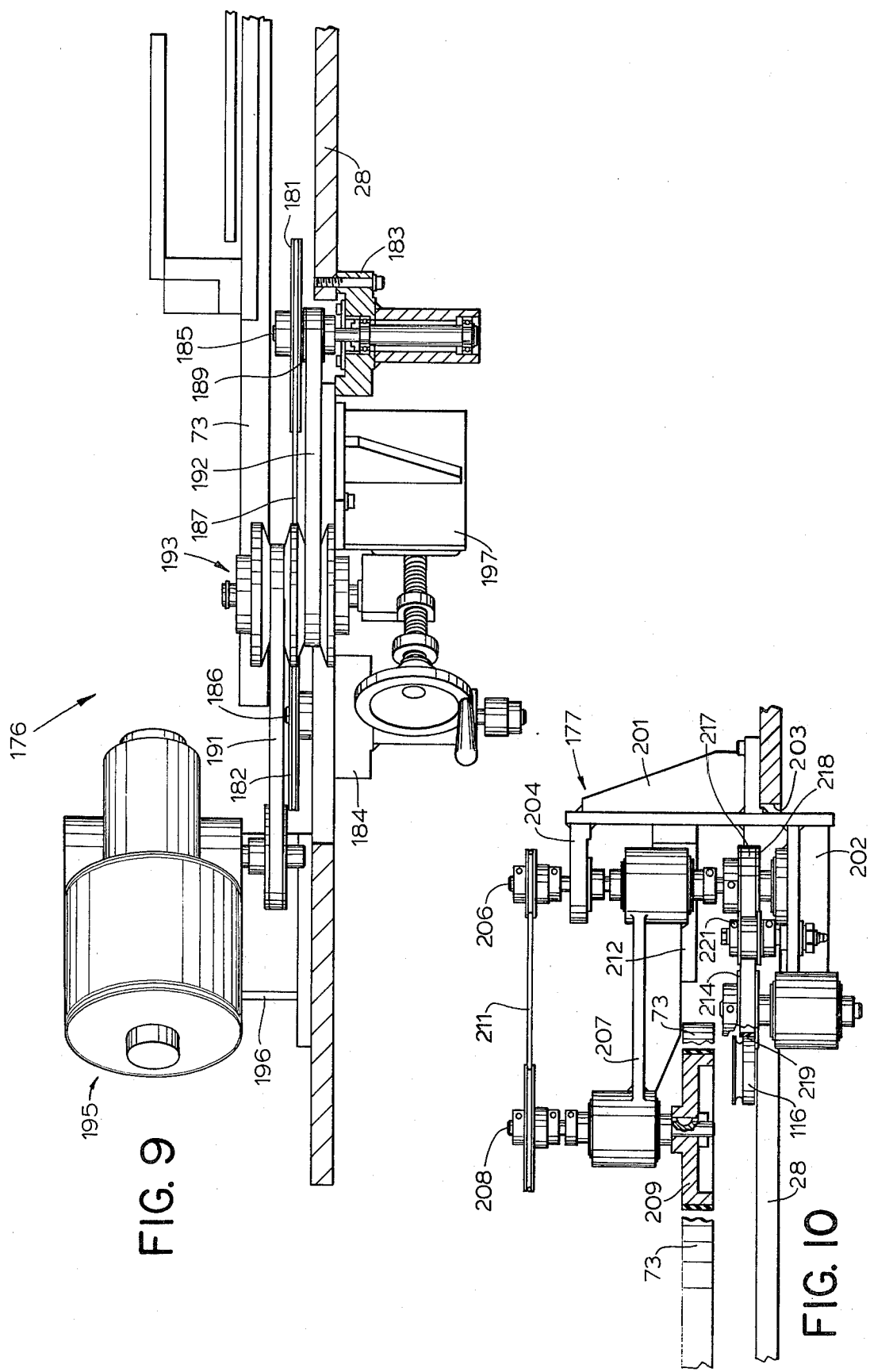

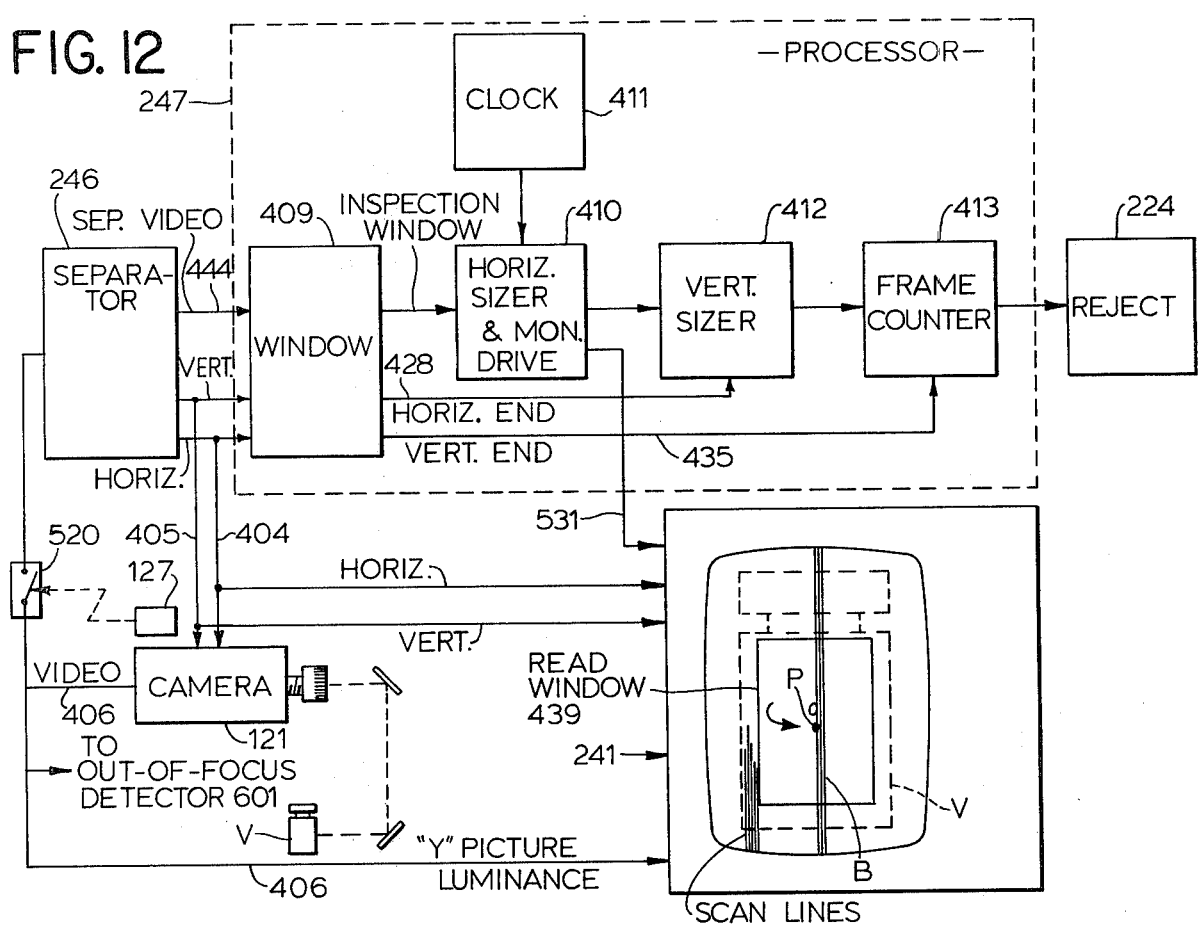
FIG. 12
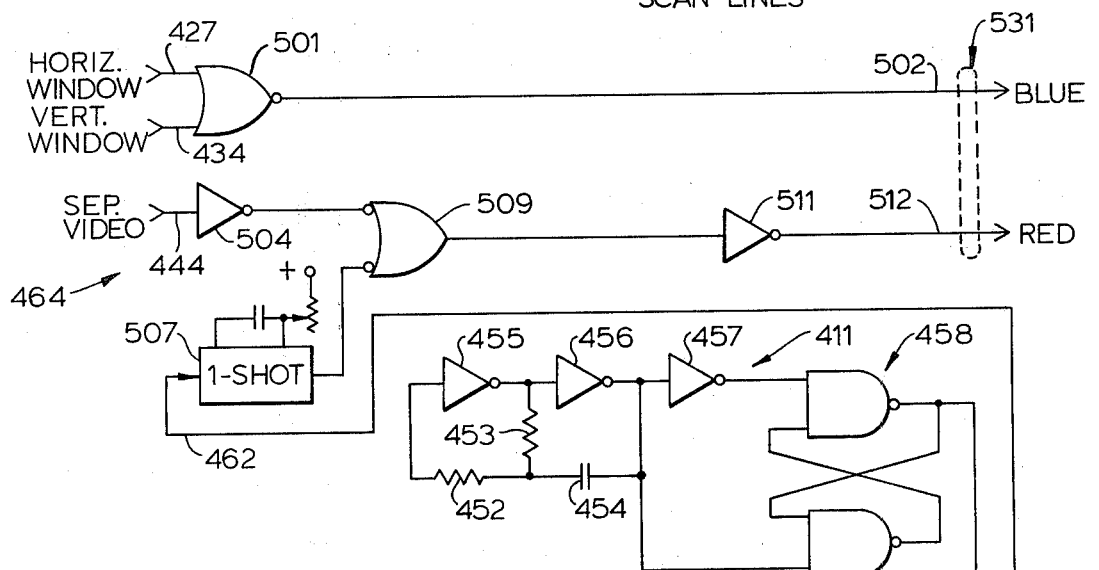
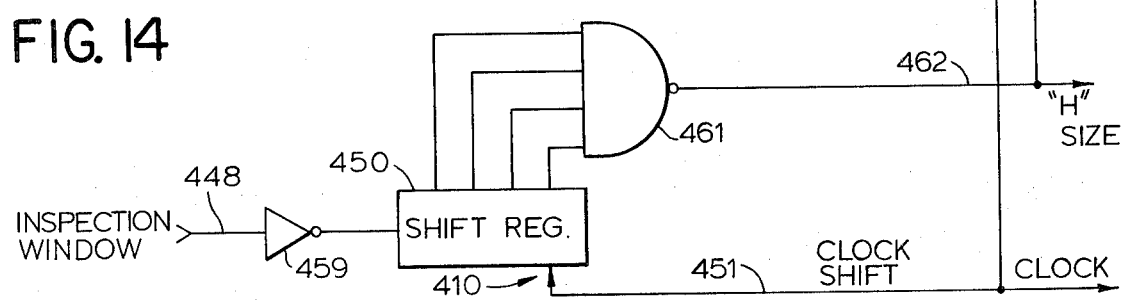
FIG. 14

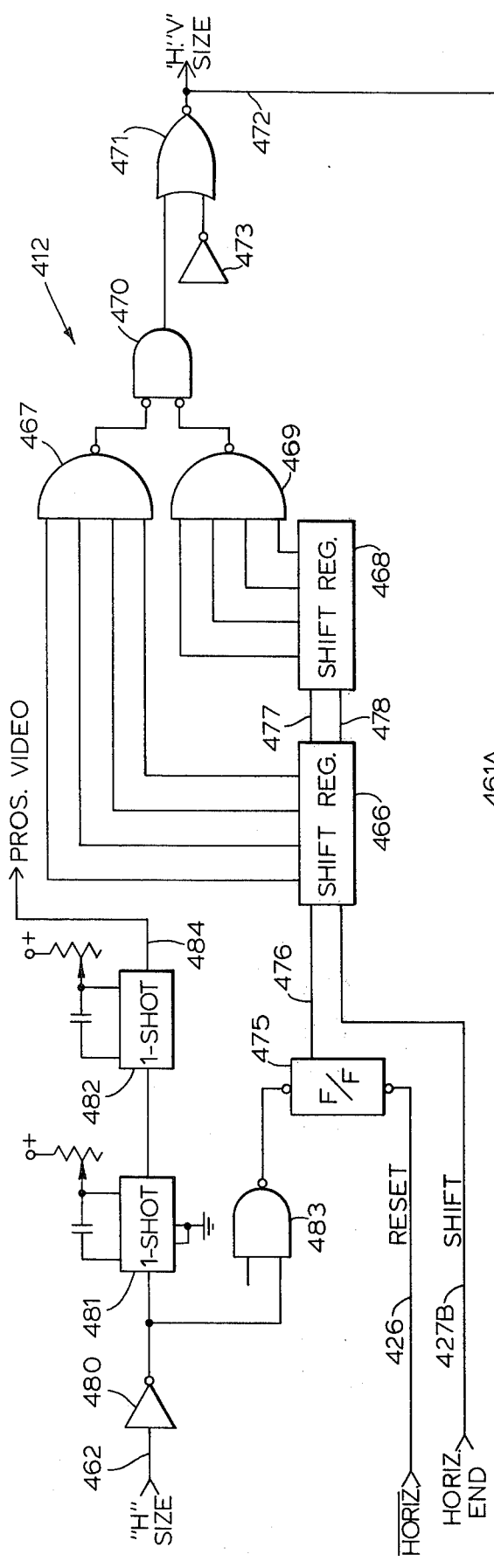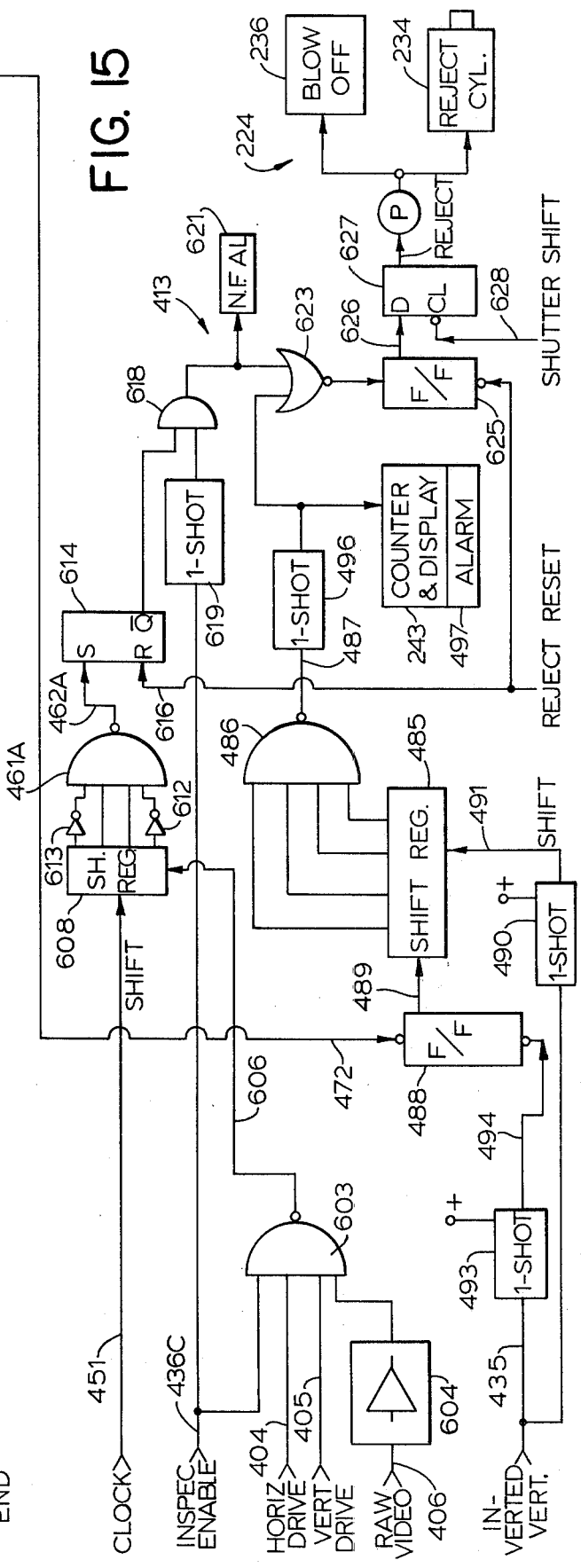
FIG. 15

INSPECTION SYSTEM

FIELD OF THE INVENTION

This invention relates to an inspection system for detecting excessive particulate matter in fluid filled vials or the like, and particularly to such a system for automatically inspecting serially presented vials, particularly containing pharmaceutical liquids.

BACKGROUND OF THE INVENTION

Inspection of liquids in transparent vessels for excessive particle content has long been done manually. Typically, the vial is agitated to place its contents in motion therewithin, placed under a strong light and viewed by a human inspector who then accepts or rejects the vial. This procedure has numerous disadvantages which have long been known. For example, individual inspectors will differ from each other in visual capability and judgment as to what particle pattern or content should cause rejection of a vial. Also, such human sorting is relatively slow, thus requiring a relatively high ratio between number of inspection man hours per quantity of vials inspected. Further, inspector fatigue tends to develop early in an inspection run, increasing the number of errors in acceptance and rejection of vials.

In view of these and other disadvantages of direct human inspection, attempts have been made over the years to provide automatic apparatus for carrying out the inspection of vials without need for human handling or viewing of the vials. However, insofar as we are aware, none of these prior machines has been entirely acceptable or satisfactory, especially for rapid yet highly reliable inspection for particle content, particularly where the threshold for acceptable particle content is very low in terms of number and small size, for example in inspection of pharmaceutical liquids containing vials. Indeed, in many instances in the pharmaceutical industry, human inspectors, despite disadvantages thereof, are still used as the vial content inspection device, and in preference to available to automatic inspection machines.

Accordingly, the objects of this invention include providing:

An inspection system for detecting excessive particulate matter in serially presented liquid filled vials or the like.

An inspection system as aforesaid capable of moving vials in series reliably and with minimum shock past serially arranged stations for spinning, inspecting and if necessary rejecting such vials, wherein a relatively compact machine is maintained despite movement of television cameras and light sources along with corresponding vials over such spin and inspection segments of vial travel.

A system as aforesaid in which inspection of each vial is carried out by a low persistance black and white closed circuit television camera, in which significant particles in the swirling vial liquid are detected by circuitry which assesses the width, height and duration of video disturbances resulting from such a particle, and wherein a closed circuit color television monitor is connected to display different system operating parameters in different colors for both set up and operation of the system.

A system as aforesaid which is operable with one or plural camera incorporating inspection units, wherein up to a first plurality of cameras may time share a single processor circuitry unit and monitor, and wherein up to a second and larger plurality of cameras may time share two processing circuitry units and a single monitor.

A system as aforesaid capable of detecting even very small particles in liquid filled vials and doing so in a reliable manner.

Other objects and purposes of this invention will be apparent to persons acquanited with apparatus of this general type upon reading the following specification and inspecting the accompanying drawings.

BRIEF DESCRIPTION OF THE DRAWINGS

FIG. 9 is an enlarged sectional view taken on the line IX—IX of FIG. 8.

FIG. 10 is an enlarged, partially broken, sectional view substantially taken on the line X—X of FIG. 8, with four evenly circumferentially spaced clamp assemblies shown in solid line with optional additional clamp assemblies shown in broken line.

FIG. 12 is a block diagram of the inspection circuitry of the system embodying the invention, shown in connection with a single camera.

FIG. 14 is a circuit diagram of the clock and horizontal sizer and monitor drive circuits of the processor of FIG. 12.

FIG. 15 is a circuit diagram of the vertical sizer and frame counter of the FIG. 12 processor, with a focus monitor.

Figure 2:
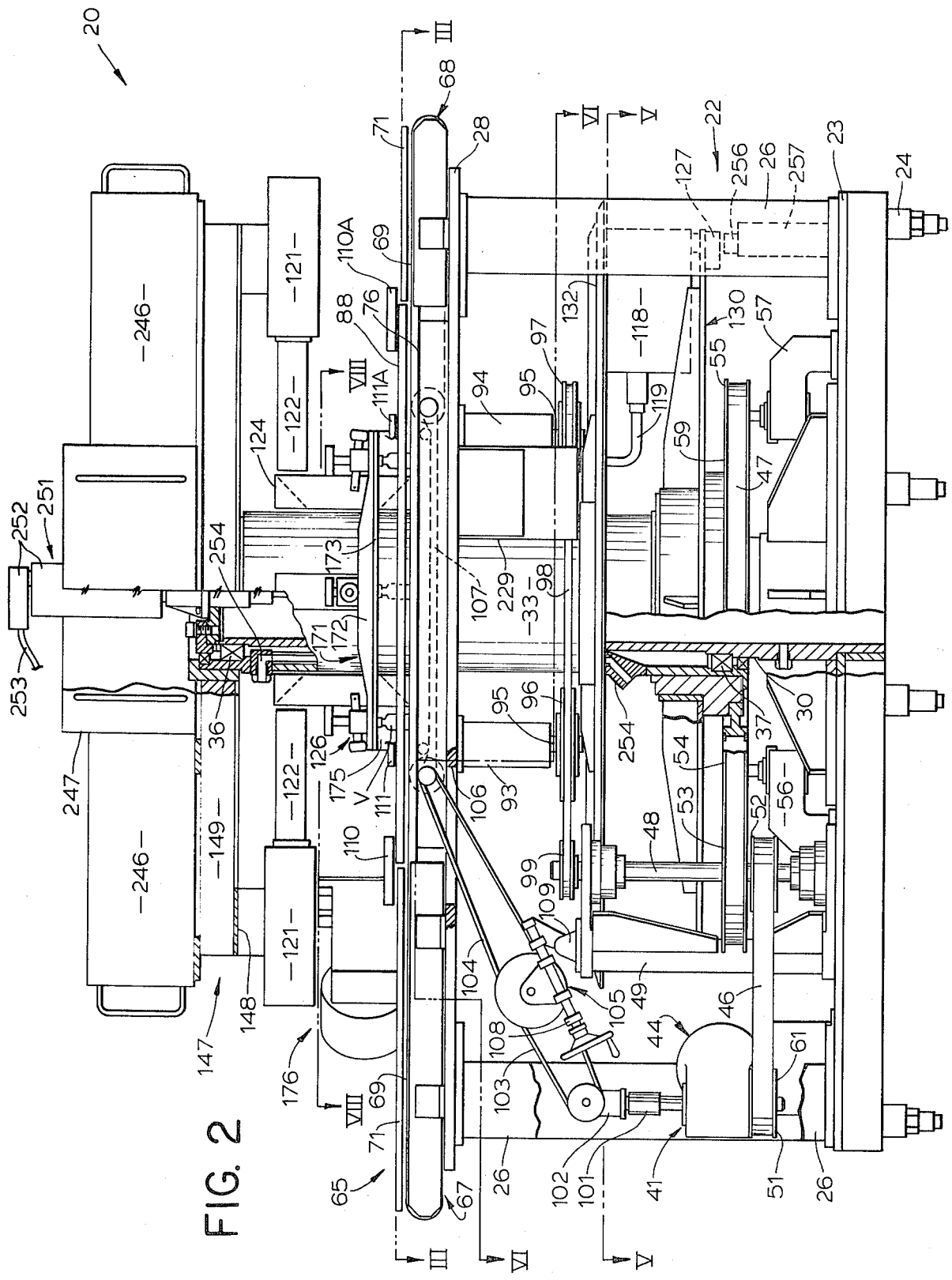
FIG. 2 is an enlarged, partially broken front view of the FIG. 1 machine.

Certain terminology will be used in the following description for convenience in reference only and will not be limiting. The words "up", "down", "right" and "left" will designate directions in the drawings to which reference is made. The words "front" and "rear" will refer to the front of the machine as seen in FIG. 2 or to the direction of vial flow through the machine as indicated by the arrows "A". The words "in" and "out" will refer to directions toward and away from, respectively, the geometric center of the device and designated parts thereof. Such terminology will include derivatives and words of similar import.

SUMMARY OF THE INVENTION

The objects and purposes of the invention are met by providing an inspection system for detecting excessive particulate matter in serially presented liquid filled vials or the like. Vials fed by an in-feed star wheel onto a rotating vial deck are subsequently removed by an outfeed star wheel, the vial deck and wheels having the same number of vial locations and vial orbit speed. At successive segments of the vial deck orbit, each vial is clamped coaxially on a spinnable puck, spun momentarily about its own axis to swirl the liquid therein, inspected for particle content and unclamped. Further rotating decks carry circumferentially arranged television cameras and lights above, and below, respectively the vial deck. Each camera looks radially inward, downward and radially outward, through a periscope orbiting therewith, to inspect any corresponding vial. Light from a corresponding light source passes radially inward then axially, through a fiberoptic member and transparent portion of the puck, to bottom light the vial. Black and white, low persistance television cameras are used. Video from a given camera inspecting the swirling contents of its corresponding vial, is applied to a separation unit which isolates the video corresponding to the swirling particles in the vial and passes such video portion to a processor unit which establishes a read window electronically mapping a central portion of the vial under inspection and in a series of steps detects any particles of interest in the vial and upon such detection triggers a reject unit operable to reject a vial having an unacceptable particle content.

A color CCTV monitor is connected to display in different colors the read window, moving particles and, where a significant size particle has been detected, an overlying highly visible bar. Switching controlled by the orbital location of the rotating cameras permits a single separator-processor and monitor to handle video from several cameras, or a pair of separator-processor units and a monitor to handle video from more cameras (e.g., twenty) on a time sharing basis.

DETAILED DESCRIPTION

Figure 1:
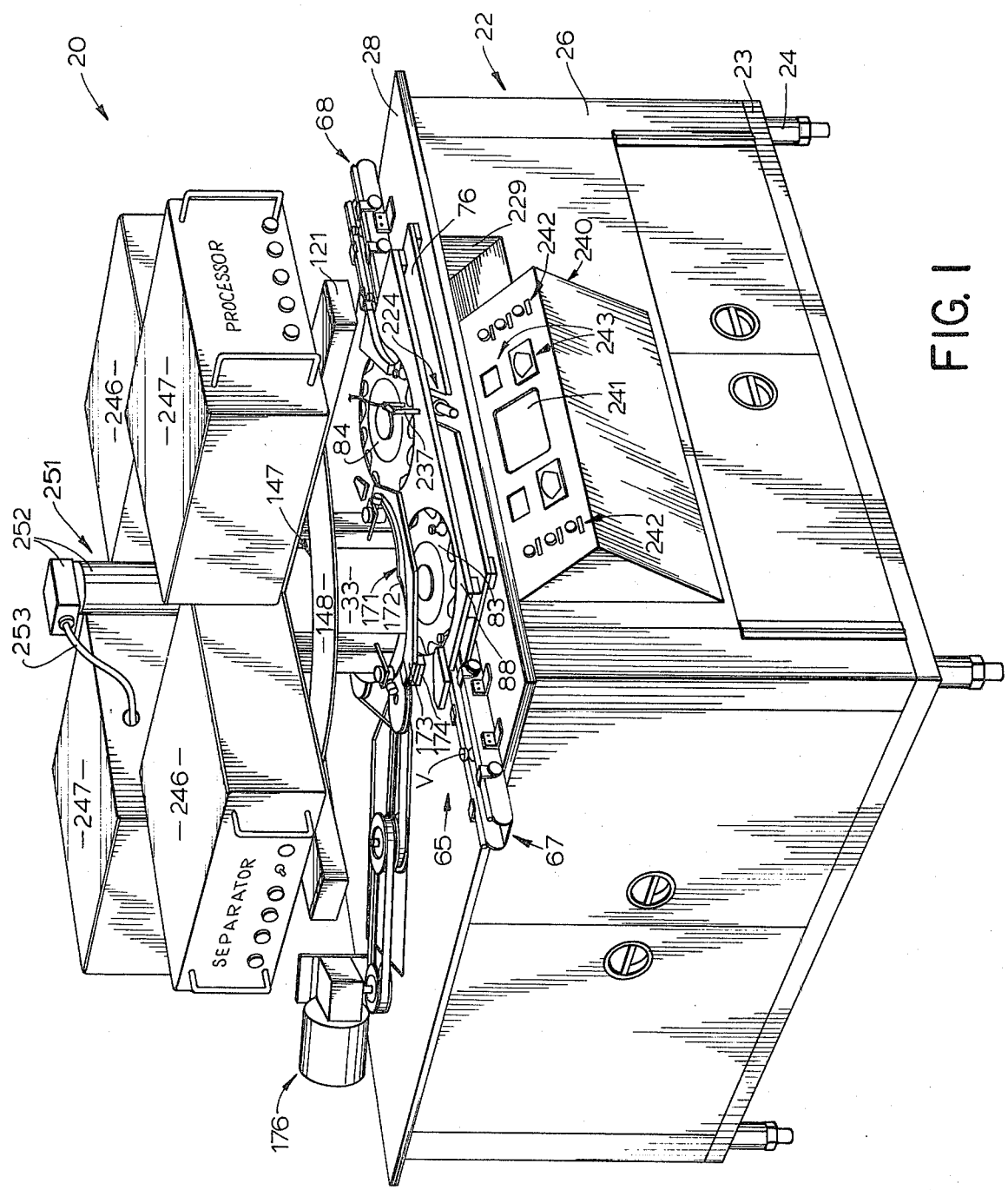
FIG. 1 is pictorial view of a machine embodying the invention.

FIG. 1 discloses an inspection apparatus 20 embodying the present invention. The apparatus 20 includes a frame 22 comprising a horizontal, preferably rectangular base 23 supported as by adjustable feet 24. Plural uprights 26 are fixed near the periphery of the base 23 and fixedly support a substantially horizontal, preferably rectangular table 28 in spaced relation above the base 23.

A hollow inner post 30 (FIG. 2) is fixed on the base 23 near the center thereof and extends upward through an enlarged opening 31 (FIG. 7) in the table 28.

A rotatable substantially cylindrical outer shell 33 coaxially surrounds the inner post 30 and extends from near the base 23 substantially to the top of the post 30. Axial-radial thrust bearings 36 and 37 carry the upper and lower ends of the shell 33 on the post 30, leaving an annular space 38 therebetween.

A rotational drive system 41 (FIGS. 2 and 5) is actuable for positively and continuously rotatable driving the outer shell 33 at a preselected constant speed. The rotational drive system 41 here includes motor means rotatably driving the shell 33 through two orbital loop means. In the embodiment shown, the motor means comprises a motor-speed varying unit 44 fixedly mounted on base 23. The orbital loop means may comprise a chain drive but preferably, and as shown, comprises toothed belts 46 and 47 cooperating through an upstanding rotatable jack shaft 48. An upstanding bracket 49 is fixedly carried on the base 23 and has bearings rotatably supporting the jack shaft 48 near its upper and lower ends. Pulleys 51 and 52 respectively fixed on an output shaft of the motor-reducer unit 44 and jack shaft 48 drive the jack shaft through the belt 46. A pulley 53 fixed on the jack shaft 48 drives the belt 47. Positioning idler pulleys 54 and 55 are located substantially chordally of, and on opposite sides of the shell 33 and are rotatably supported as at 56 and 57 in fixed location above the base 23. A driven pulley 59 is coaxially fixed on the lower end portion of the shell 33 in coplanar relation with pulleys 53, 54 and 55. The belt 47 orbits around pulleys 53, 54 and 55 and engages the shell pulley 59 with its outer face to positively rotatably drive the shell 33. The belt 47 is both externally and internally toothed, the belt 46 is at least internally toothed and at least the corresponding driving and driven pulleys 51, 52, 53 and 59 are correspondingly toothed for positive driving. Belt tension may be maintained, as desired, here for example by a tensioning roller 61 engaging belt 46 and pivotally adjustably mounted with respect to the base 23. Supports 56 and 57 may be laterally adjustably mounted on base 23 to control the tension of belt 47.

The inspection apparatus 20 includes a vial, or bottle, transport system 65 (FIGS. 1-3) immediately above the table 28. The vial transport system 65 includes laterally aligned input and output vial conveyors 67 and 68 of endless belt type mounted on table 28 in sidewardly aligned relation ahead of the rotatable shell 33. Vials entering and exiting the machine ride atop the upper surfaces 69 of conveyors 67 and 68 between fixed guides 71.

An annular vial deck 73 (FIG. 7) is coaxially fixed on the rotatable shell 33 above the table 28 and has an upper, vial carrying surface 74 in the plane of the vial surfaces 69 of the input and output conveyors.

A vial plate 76 (FIGS. 1-3 and 7) is spaced above and fixedly mounted on table 28 such that its upper surface 77 is coplanar with the vial support surfaces 69 and 74 of the conveyors 67 and 68 and the rotatable vial deck 73. The vial plate 76 has oppositely opening side notches 78 and 79 into which the opposed ends of the vial conveyors 67 and 68 extend and a rear opening semicircular notch 81 closely receiving the front edge of vial disk 73. The front edge portion of the vial conveyors 67 and 68, adjacent their opposed inner ends, lie closely adjacent the forward portion of the vial plate 76. Thus, an essentially continuous path is provided by which vials can be advanced from infeed conveyior 67 slidably along vial plate 76, onto rotating vial deck 73 for a substantial portion of a rotation and thence once again onto vial plate 76 for slidable advancement onto the outfeed conveyor 68.

The vial transport system 65 further includes means for advancing the vials slidably on vial plate 76 along the route described. Particularly, peripherally toothed infeed and outfeed star wheels 83 and 84 (FIGS. 1, 3 and 7) are disposed immediately above the level of conveyors 67 and 68, vial table 76 and vial disk 73. The star wheels 83 and 84 are sidewardly adjacent each other, respectively overlap the inboard ends of conveyors 67 and 68, and both overlap adjacent front portion of the rotatable vial disk 73.

The teeth 86 of the star wheels are of depth corresponding to the diameter of a vial V to be engaged thereby and have substantially radial trailing flanks and chordally extending leading flanks to facilitate capture and release of vials by the star wheels combined with positive circumferential advancement of vials by the star wheel.

A platelike, substantially T-shaped, central vial guide 88 (FIGS. 1 and 3) is fixed with respect to table 28 in close spaced relation above vial plate 76. Central vial guide 88 is substantially coplanar with the star wheels 83 and conveyor guide 71, all of which are vertically located to engage an intermediate sidewall portion of each vial. Sidewardly opening notches 90 and 91 (FIG. 3) are semicircular and closely receive the star wheels to guide vials in a sinuous path from infeed conveyor 67 to rotating vial deck 73, and then from the latter to outfeed conveyor 68.

Bearing units 93 and 94 (FIGS. 2 and 7) are fixed to and depend from table 28. Such bearing units rotatably support vertical shafts 95. The upper ends of shafts 95 fixedly, but preferably circumferentially adjustably, mount the corresponding star wheels 83 and 84. A positive drive member, here an externally toothed pulley, is fixed to the bottom end of each shaft 95, as indicated at 96 and 97 in FIGS. 2 and 6. Pulleys 96 and 97 are positively driven through a belt 98 from a drive pulley 99 fixed atop jack shaft 48. In this manner, the rotational speeds of star wheels 83 and 84 and rotatable bial deck 73 are synchronized such that the peripheral speed of the vial engaging portions of the star wheels and vial deck are the same. Moreover, adjustment of the angular orientation of each of the star wheels with respect to its shaft 95 permits circumferential fixing of vial locations on the vial plate 76.

Motor unit 44 here is also used to drive the vial conveyors 67 and 68. Particularly, the motor unit 44 includes an upstanding power takeoff 101 (FIG. 2) capped by a right angle drive 102 which rotatably drives infeed conveyor 67 through a pair of belts 103 and 104 coupled by an adjustable ratio device 105, here a Model No. 145HRB-2 made by the Hi-Lo Manufacturing Copany of Minneapolis, Minn., such that the speed of the belts 67 and 68 can be set to somewhat exceed that of the star wheels 83 and 84 to insure full loading of infeed star wheel 83 with vials and adequate clearing of outfeed star wheel 84 of vials. The table 28 is slotted at 106 so that the belt 104 can drive the corresponding driven pulley on infeed conveyor 67. The opposed end shafts of infeed and outfeed conveyors 67 and 68 are coupled by a further chain drive 107 such that the former drives the latter.

Thus, by rotative adjustment of the screw 108 (FIG. 2) of adjustable ratio device 105, which device is mounted at 109 atop bracket 49, the speed of the conveyors 67 and 68 can be varied with respect to that of the star wheels 83 and 84 and vial deck 73.

Transfer guides 110 and 111 (FIG. 3) are fixed with respect to and located above the table 28 in closely overlapping relation with infeed star wheel 83. The transfer guides 110 and 111 each define, with the opposed portion of the central vial guide 88, a vial path from input conveyor 67 into the toothed periphery of wheel 83, or out of such wheel and onto the rotatable vial deck 73. Similar transfer guides 110A and 111A overlie the outfeed star wheel 84 and coact with substantially opposed portions of the central vial plate 88 to channel vials out of the outfeed star wheel and onto outfeed conveyor 68, and to channel vials from the rotatable vial deck 73 into the outfeed star wheel.

Figure 4:
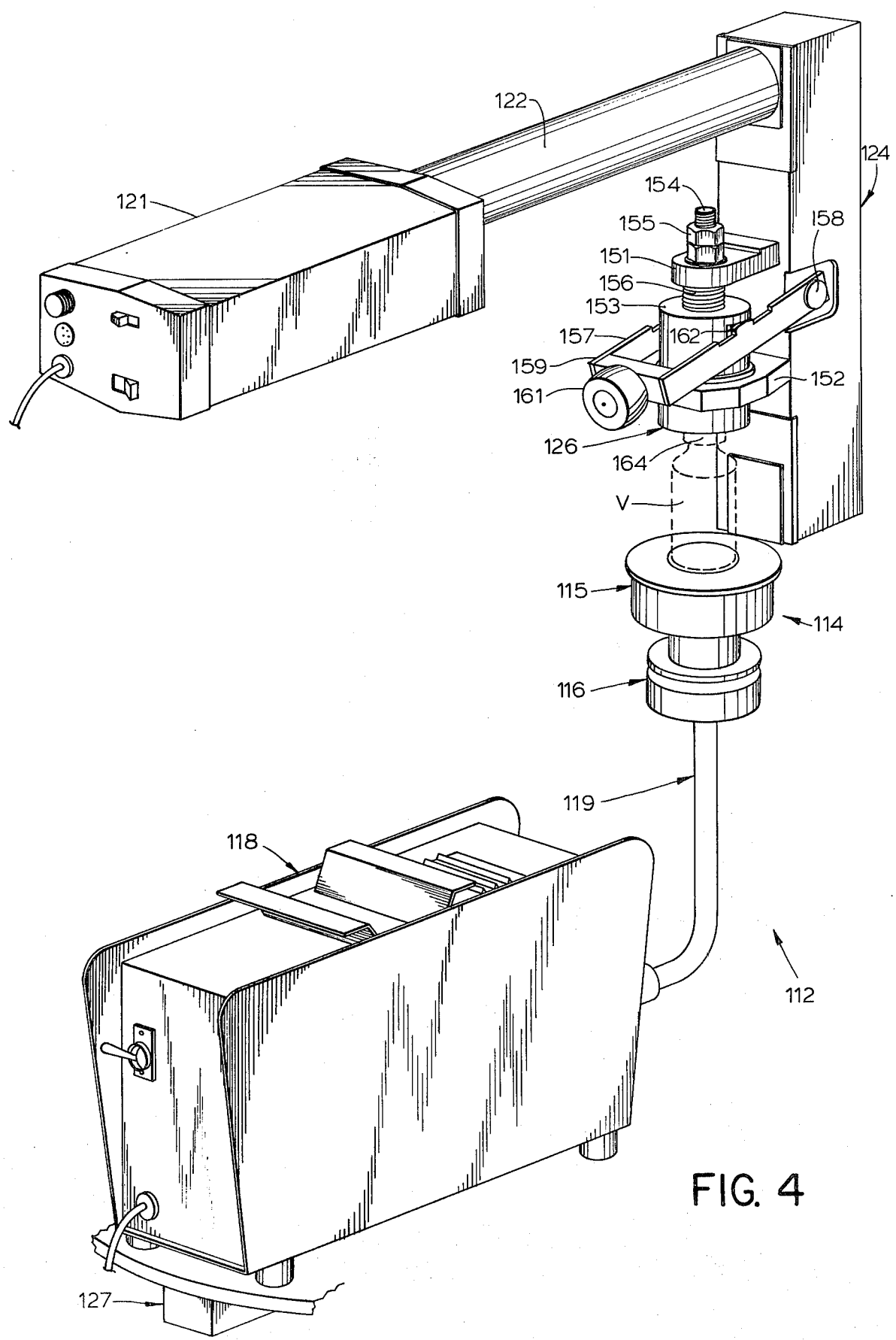
FIG. 4 is an enlarged pictorial view of one of the inspection units of the FIG. 1 machine.

Rotatable shell 33 supports a plurality of inspection units 112, one of which is shown in FIG. 4. The inspection units are preferably identical to each other, evenly circumferentially distributed on shell 33 and of even number. In the embodiment shown, four inspection units are provided. However, this number can be increased, for example, up to twenty.

Figure 7:
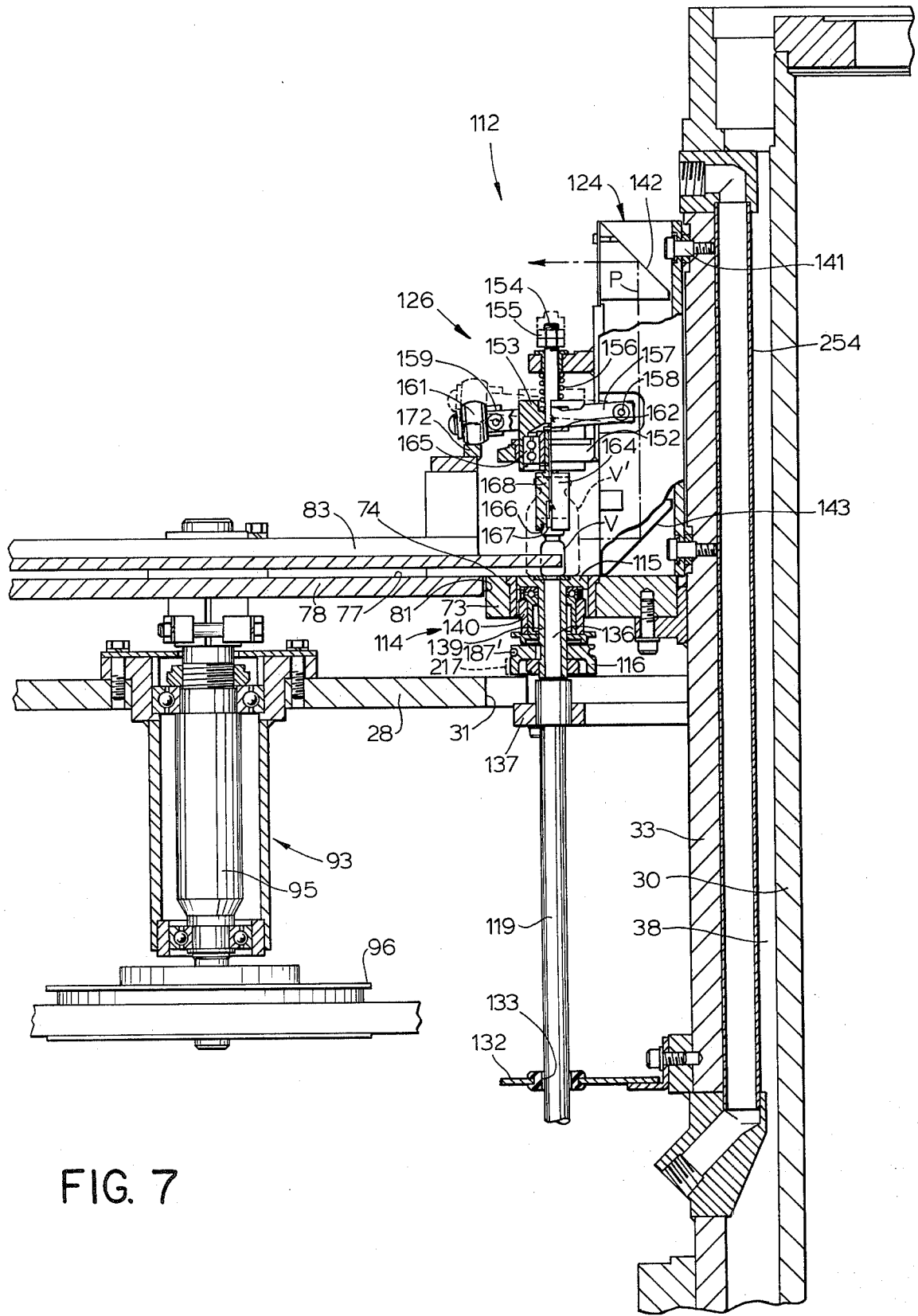
FIG. 7 is an enlarged, partially broken vertical cross sectional view substantially as taken on the line VII—VII of FIG. 3.

Each of the circumferentially distributed inspection units 112 includes a hollow puck assembly 114 mounted on and freely rotatable with respect to the vial deck 73. The puck assembly includes a vial support puck 115 mounted flush with the top of the rotatable vial deck 73, as seen in FIG. 7, and a spin-and-brake pulley 116 pendently fixed to the puck 115.

Each inspection unit 112 further includes a light source 118 disposed below the vial deck and aimed radially inward toward the shell 33. A fiber optic light conductor 119 extends radially inward from each light source 118 and then bends and extends upward to the corresponding puck assembly 114 to eliminate a vial V concentrically supported on the puck 115.

Each inspection unit 112 further includes a television camera 121 spaced above the light source and having optics aimed radially inward toward shell 33 along an optic path surrounded by a light excluding tube 122. A periscope 124 is vertically supported on the rotatable shell 33 and has upper and lower ends disposed radially inboard of the camera tube 122 and vial V, respectively, such that the camera 121, while aimed radially inward, effectively looks radially outward toward the vial V.

Each periscope 124 supports a vial clamp and upper bearing assembly 126 actuable by rotation of the shell 33 for alternatively gripping and releasing the top of the corresponding vial V. Also at each inspection unit is provided a magnetic reed switch 127.

Figure 5:
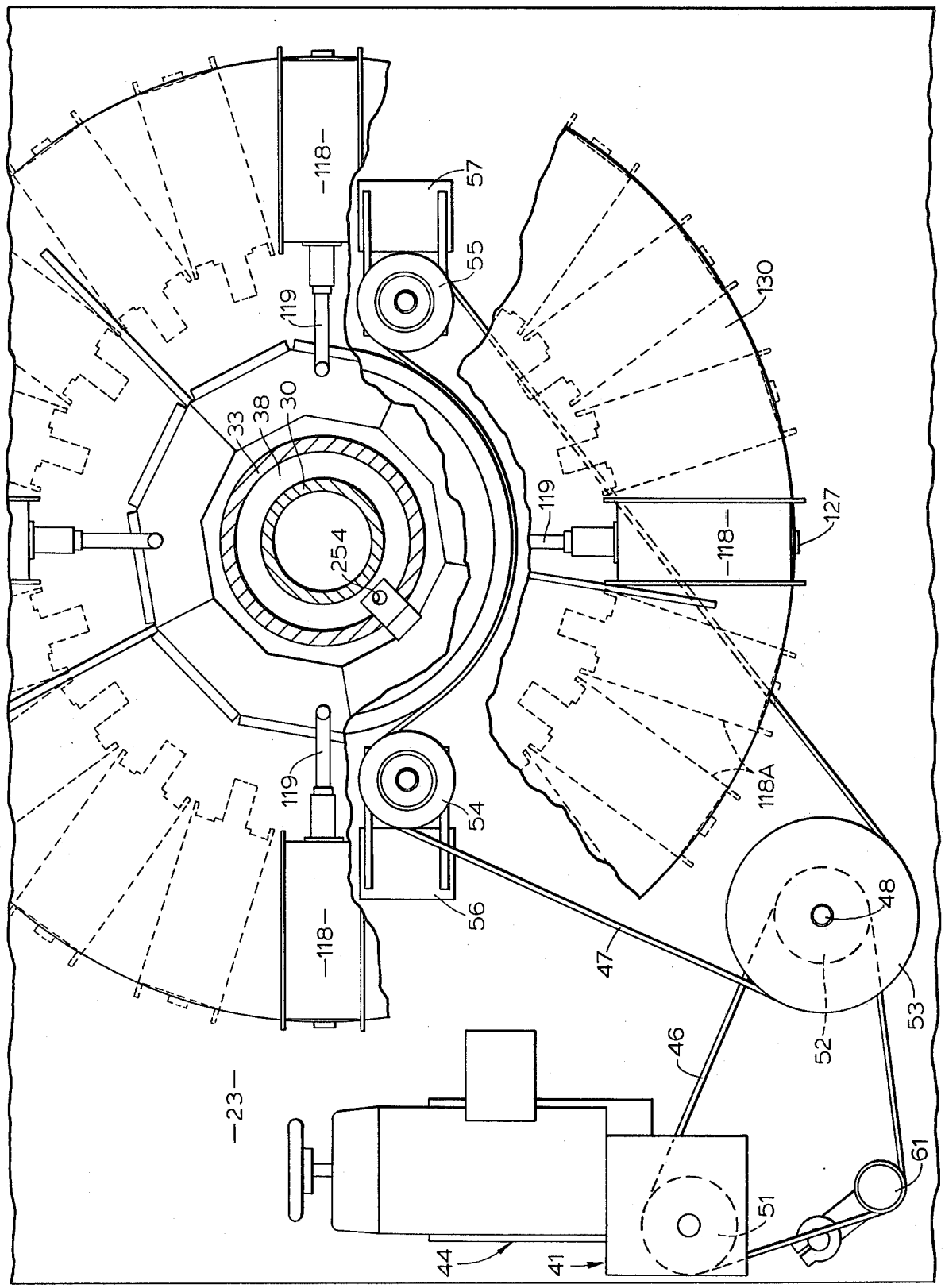
FIG. 5 is an enlarged, partially broken sectional view substantially taken on the line V—V of FIG. 2.

The rotatable shell 33 (FIG. 2) carries a vertically spaced series of decks which support corresponding portions of the plural inspection units 112. The lowest of these, the light source deck 130, is fixed to and coaxially surrounds the shell 33 immediately above the shell-driven pulley 59. The light sources 118 are fixed upon and evenly circumferentially distributed on the light deck 130, as seen in FIG. 5, wherein the light sources for the four inspection unit arrangement are shown in solid lines with the additional light sources for a twenty inspection unit system indicated in broken lines, as at 118A. The corresponding reed switches 127 (FIG. 2) are fixed beneath the light deck 130.

A further deck, hereinafter referred to as the drip shield 132, is fixed to and extends radially from the shell 33 sufficiently to overhang the light sources 118. The drip shield 132 is disposed immediately above the light sources 118 and below the star wheel drive belt 98. Circumferentially spaced openings 133 in drip shield 132 are preferably grommeted and admit therethrough the upwardly extending leg of the fiber optic 119 from each light source. Thus, a plurality of circumferentially distributed fiber optics 119 extend upward along the shell 33. The upper end of each fiber optic 119 optically couples to but is spaced beneath a short transparent plastic (e.g. lucite) rod 136 secured in and filling the central opening of the corresponding puck assembly 114, as seen in FIG. 7. The fiber optic upper end portions here are fixedly supported by an annular fiber optic deck 137 fixedly surrounding the shell 33 beneath vial deck 73.

The puck 115 incorporates a hollow central shaft 139 and is rotatably supported in an opening in the vial deck 73 by a bearing unit 140. The spin-and-brake pulley 116 is fixed to the puck 115 through hollow shaft 139, such that spinning or braking of the pulley 116 correspondingly spins or brakes the puck 115 fixed thereto. A vial V or V' seated coaxially atop the puck 115 receives light through its transparent bottom wall from the filler rod 136 of puck shaft 139 and fiber optic 119. If desired, the lighted area of the vial bottom can be controlled by the bore size of a washer coaxially recessed in the top of the puck 115.

The periscope 124 (FIG. 7) is fixed to the side of shell 33, as by screws 141, and extends down to the vial deck 73. Reflecting means, here prisms 142 and 143, fixed in the upper and lower ends of the periscope 124, provide an optical path P which extends radially inwardly from the illuminated vial V, thence upwardly, thence radially outwardly to the corresponding camera 121. By use of the radially inwardly directed camera and light sources and the resultant bending of the light path thereof provided by the fiber optics 119 and the periscopes 124, the breadth of the apparatus 20 is minimized while permitting a large number of inspection units (e.g. twenty) in the same apparatus.

The cameras 121 for the several inspection units 112 are pendently fixed to a camera deck 147 fixed to and radially extending from the upper end portion of the rotatable shell 33 in spaced relation above the vial deck 73 and table 28. In the embodiment shown, the camera deck 147 is wheellike, having a peripheral rim supported by plural radially extending spokelike members 149.

Returning to the vial clamp assemblies 126 of the inspection units 112, each includes a vertically spaced pair of platelike bracket members 151 and 152 (FIGS. 4 and 7) fixed to and extending outboard from the corresponding periscope 124. A hub member 153 is vertically slidable in and extends through an opening in the bracket 152. The hub 153 has a reduced diameter coaxial upper portion 154 which is slidably arranged in and extends upward through an opening in bracket 151. Stop notch 155 threadedly engaging the upper end of hub extension 154 adjustably limits downwardly movement thereof. A coil spring 156 on hub extension 154 biases the hub downward from the bracket 151.

Arms 157 are pivoted at 158 on opposite sides of the periscope 124 and extend outboard therefrom on opposite sides of the hub 153. The outboard ends of pivot arms 157 are joined by a bar 159 rotatably supporting a cam follower roller 161. The intermediate portions of the arms 157 pivotally and slidably engage therebetween the opposite sides of the hub 153, as by reception in shallow tangential slots 162 in such hub, such that upward swinging of the camming roller 161 raises the hub 153 against the force of spring 156.

The bottom of hub 153 is coaxially recessed to receive and support a downwardly extending chuck member 164. A bearing 165 secured in the hub recess rotatably locates the chuck 164. The bottom of chuck 164 is provided with a frustoconical, coaxial recess 166 (FIG. 7) sized for a vial centering, wedged fit on the capped upper end of a vial V carried on corresponding puck 115, in response to downward urging by spring 156. Preferably, a knockout pin 167 is coaxially received in a central opening in the chuck 164 and is spring urged at 168 downward to bear against the top of a vial V engaged by chuck 164 so as to forcibly separate the vial from the chuck upon raising of the chuck and hub by an upward swing of the camming roller 161.

To raise and permit lowering of the chuck members 164 of the vial clamp units 126 in proper synchronism with the rotative position of each clamp assembly 126, a cam member 171 (FIGS. 2 and 8) is fixedly supported above the central vial guide 88 in concentric relation with the front portion of the rotatable shell 33. The cam member 171 comprises an upstanding cam rail 172 which curves concentrically of the front face of shell 33 in centered relation on central vial guide 88 at a radial location corresponding to that of the cam rollers 161, which cam rollers ride upon the upper surface of cam rail 172. In the embodiment shown, the cam rail extends through an angle of about 126°. The central portion of the cam rail 172 is raised and flat and the end portions (each of about 40° angular extent) form smoothly curved acceleration and deceleration ramps extending to the ends of the cam rail. The cam member 171 further includes a relatively narrow base plate which extends outward from the bottom of cam rail 172 and extends in a curved manner along the length thereof. The base plate 173 is supported at its ends and center by blocklike members 174 and 175 fixedly supported on the table 28 (as through central vial guide 88 in the case of central support block 175). Thus, during rotation of the shell 33, the vial clamp assembly 126 of each inspection unit 124 is raised as it approaches the front of the machine and the vial path to the outfeed star wheel. The cam member 171 does not lower such vial clamp assembly until same has rotated past the front central portion of the machine and to the point where the infeed star wheel has concentrically located an incoming vial V on a puck 115 of the vial deck. The cam then lowers the corresponding vial clamp assembly 126 so that the chuck 164 thereof centers the vial V on the puck 115 while urging said vial firmly downwardly thereagainst.

Figure 8:
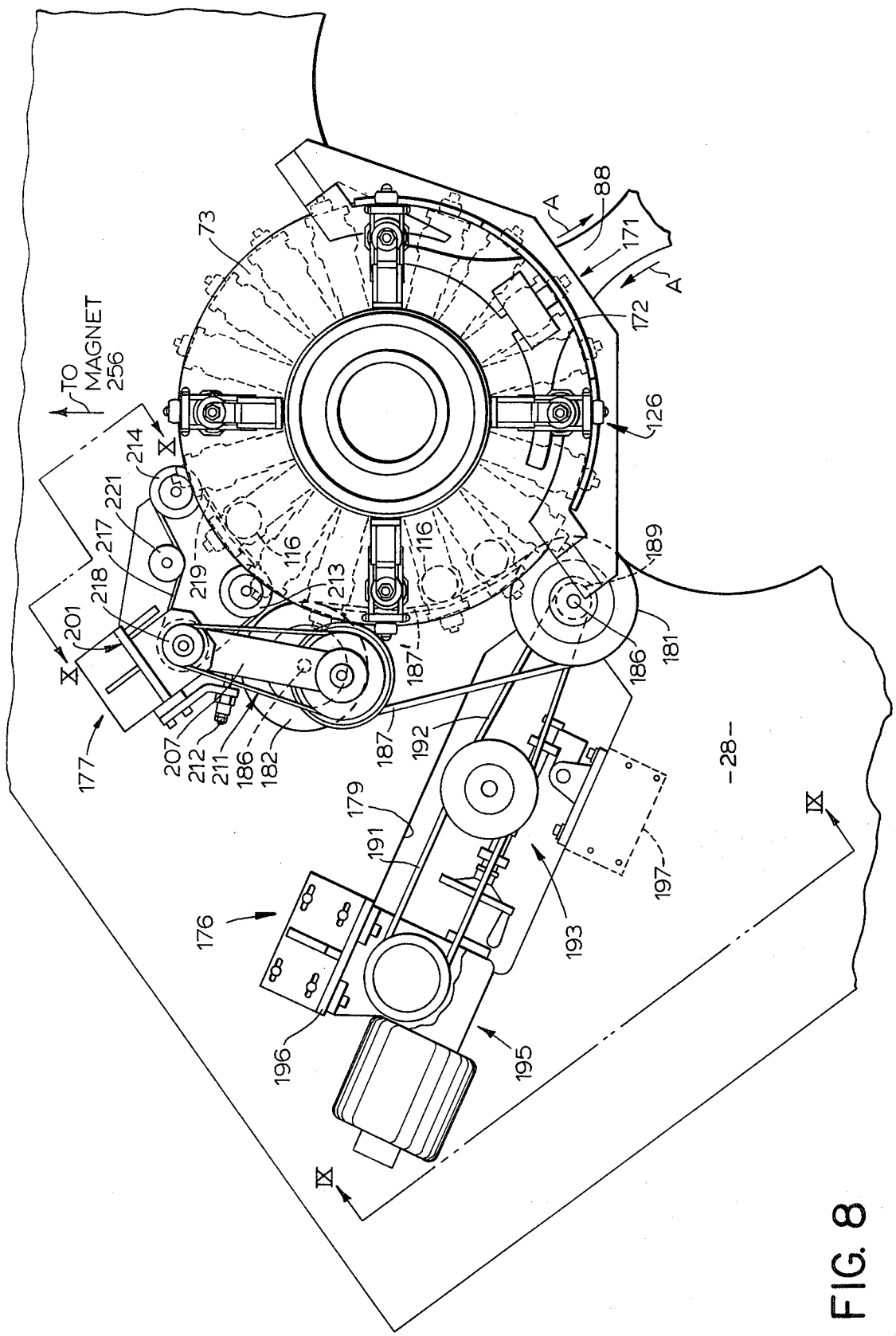
FIG. 8 is a somewhat enlarged sectional view substantially taken on the line VIII—VIII of FIG. 2 and rotated counterclockwise through about 35° for convenience in drawing.

The vial then rotates with the shell 33 and vial deck 73 beyond the infeed star wheel 83 and infeed end of cam member 171 into the rearward or detection zone of the apparatus. As seen in FIGS. 8–10, a vial spin unit 176 and a vial brake unit 177 are disposed in such detection zone of the apparatus to successively spin and brake each vial placed on the vial deck 73 by coaction with the pulley 116 of the corresponding puck assembly 114.

Table 28 is here provided with an opening 179 (FIG. 8) substantially tangential to the rotatable vial deck 73 to provide clearance space for portions of the spin unit 176.

The spin unit 176 includes a pair of puck belt pulleys 181 and 182 disposed circumferentially along and each slightly overlap vial deck 73. The pulleys 181 and 182 are vertically disposed between the vial deck 73 and fixed table 28. Suitable bearing brackets 183 and 184 pendently fixed to the table 28 rotatably support shafts 185 and 186 to the upper ends of which pulleys 181 and 182, respectively, are fixed. A circular cross-section puck spin belt 187 orbits on the pulleys 181 and 182, the outer face of belt 187 engaging successively presented spin and brake pulleys to rotate (spin) same therewith.

Puck belt pulley 181 is coshafted with and driven by the output pulley 189 of a dual belt drive system including belts 191 and 192, an adjustable ratio drive device 193 (preferably similar to device 105 above discussed with respect to FIG. 2) and a gear motor 195. Respective upstanding and depending brackets 196 and 197 support the gear motor 195 and adjustable ratio device 193. The gear motor 195 rotatably drives puck spin belt 187 through belt 191, adjustable ratio device 193, belt 192, and pulleys 189 and 181.

The vial brake unit 177 (FIGS. 8 and 10) is intended to halt the vial rotation or spinning achieved by spin unit 176 such that the vial becomes fixed with respect to the rotating vial deck 73.

The vial brake unit 177 includes a bracket 201 fixed atop table 28 and having a portion 202 extended downward through an adjacent opening 203. The lower portion 202 and an upper portion of the bracket 201 carry bearings rotatably supporting a vertical main shaft 206.

An arm 207 pivoted on main shaft 206 has a free end rotatably supporting a vertical pick-up shaft 208. A pick-up wheel 209 fixed on the lower end of pick-up shaft 208 has a frictionally surfaced periphery rotatably driven by the rim of rotatable vial deck 73. The speed of pick-up shaft 208 is thus proportional to the rotational speed of vial deck 73. Through a belt and pulley set 211 the pick-up shaft 208 rotatably drives the main shaft 206. The pick-up wheel 209 is maintained firmly against the rim of vial deck 73 by a compression spring biased plunger 212 slidably supported by an extension of bracket 201 and which bears on arm 207.

The lower portion 202 of bracket 201 extends toward the axis of annular vial deck 73 and rotatably supports a pair of flat belt idler pulleys 213 and 214 immediately adjacent the rotative path of the spin and brake pulleys 116, and more particularly the lower cylindrical skirt portions 216 thereof. A flat brake belt 217 rotatably driven by a pulley 218 rotatably fixed to the lower portion of main shaft 206 extends around idler pulleys 213 and 214 such that an intervening portion 219 of belt 217 frictionally engages and controls rotation of each passing puck pulley 216, and hence of the vial associated therewith. A belt tensioning roller 221 adjustably supported on the lower bracket portion 202 tensions the brake belt 217.

By appropriate selection of the rotative speed ratio between the friction wheel 209 and brake belt 217 indirectly driven thereby, the belt 219 brings the outward facing surface of puck pulley 116 to the same angular velocity as the axially opposed portion of the vial deck 73, i.e., halts spinning of the puck pulley 116 and associated vial with respect to vial deck 73.

By thus spinning each vial in succession with spin unit 176, liquid in the vial is caused also to spin and will continue to spin after vial spin is halted by brake unit 177. After being brought to this condition the contents of the vial can be inspected for particulate content by the associated television camera 121 and associated processing circuitry as hereafter discussed, such occurring as the vial deck 73 rotates the vial past the brake unit 177 and on toward the outfeed star wheel 84 of FIG. 3.

When such processing circuitry determine that a given vial has unacceptable contents, the vial is to be rejected, i.e. segregated from other vials passing from the apparatus. To this end, a vial rejection unit 224 (FIGS. 3 and 11) is provided below the outfeed star wheel 84 near the front of the apparatus. The rejection unit 224 includes a paddlelike trapdoor 226 laterally slidable in a recess 227 in the top of vial plate 76, the upper surfaces of trapdoor 226 and vial plate 76 being flush. In its inboard position shown, the trapdoor 226 underlies the path of vials moved by the outfeed star wheel 84 and prevents vials from dropping through an underlying opening 228 in the vial plate 76. A rejected vial hopper 229 is pendently fixed to the table 28. Upon substantially forward withdrawal of the trapdoor 226, a vial thereatop drops by gravity through opening 228 and an aligned opening 231 in table 28 into the reject hopper 229. The sliding motion of the trapdoor 226 is guided by a guide block 232 fixed to the central vial guide 88 and which slidably engages longitudinal slot 233 in the trapdoor 226. A drive device, here a double acting air cylinder 234 mounted at 235 on vial plate 76, has its piston rod secured to the trapdoor at 238 for opening and closing such trapdoor upon command of inspection circuitry hereafter discussed.

To assure reliable dropping of a rejected vial into the reject hopper 229, a downwardly directed blow off nozzle 236 is mounted by a bracket 237 atop the central vial guide 88 and is actuable simultaneously with trapdoor cylinder 234 by the mentioned processing circuitry for applying a jet of air from a conventional source P of air under pressure, downwardly on to a vial V to be rejected to propel same downwardly into the reject hopper as the trapdoor 226 is withdrawn.

A control panel 240 (FIG. 1) preferably is mounted on the frame 22 at a position convenient to a human operator. The control panel 240 preferably includes a television monitor 241 and suitable controls generally indicated at 242 for operating the apparatus. If desired further information read-out devices, as generally indicated at 243, may be provided and these may include counter read-outs for indicating the number of vials processed and rejected, etc.

Circuitry units 246 and 247 are conveniently carried on the upper side of the camera deck 147. In the preferred embodiment shown, the circuitry unit 246 receives camera video and separates, for further processing in circuitry unit 247, that portion of the video signal corresponding to swirling particles in the vial being scanned by a given camera. The processor unit 247 then determines if the particle content of such vial is excessive, and if so causes the rejection unit 224 to drop the vial into the rejection hopper 229.

One each of units 246 and 247 will suffice when the apparatus 22 is equipped with only a few inspection units 124, such as the four shown in FIGS. 1 and 2. However, when a substantial number of inspection units are provided on the same apparatus, e.g. twenty, two each of circuitry units 246 and 247 are provided as seen in FIG. 1. In that instance, one pair of units 246 and 247 sequentially handles the video output of the odd numbered cameras 1, 3, 5, etc. and the remaining pair of circuitry units 246 and 247 handles the video output of the remaining, even numbered cameras 2, 4, 6, etc.

In the preferred embodiment shown, the units 246 are preferably commercially available units available under Model No. PEP 700 from Princeton Electronics Products, Inc. of North Brunswick, N.J.

To provide for electrical interconnection between the fixed and rotating components and to supply operating potential to rotating components, a conventional multi-circuit vertical mercury-wetted slip ring assembly 251 is coaxially affixed atop the hollow inner post 30 and extended downward thereinto. The slip ring assembly may be a Model LS-122-12 manufactured by CER/-CON Corporation of Madison, Wisconsin. The slip ring assembly 251 here includes an upper and outer rotating portion 252 from which suitable cabling, a portion of which is indicated at 253, leads appropriate electrical conductors to rotating electrical components of the apparatus, including circuitry units 246 and 247, the cameras 121, the light sources 118, etc. The central and lower portion 254 (FIG. 2) of slip ring assembly 251 provides fixed electrical cabling, not shown, which preferably leads downward through hollow inner post 30 and out the bottom of the apparatus for connecting to fixed portions of the apparatus, including control panel 240, thus establishing electrical communication between fixed and rotating components of the apparatus.

Conduits 254 (FIG. 2) located in the annular space between the fixed inner post 30 and rotating outer shell 33 extend vertically from below splash deck 132 upward to just below the camera deck 147 and open outward through the periphery of shell 33 for routing electrical wiring for the light sources 118 and reed switches 127. The reed switches 127 are sequentially tripped as they rotate with the shell 33 by magnet means (e.g., a small permanent magnet) 256 (FIG. 2) supported as by a bracket 257. Conveniently, each reed switch 127 is disposed below its corresponding camera 121 (in a manner identical for all cameras and their reed switches 127) and magnet 256 is circumferentially located on fixed base 23 adjacent the end of the vial spin (and brake) segment of the vial deck orbit, as generally indicated by the arrow in FIG. 8 (the magnet 256 being shown circumferentially displaced in FIG. 2 for convenience in illustration). Thus the reed switch 127 for each camera 121 will be tripped by magnet 256 when the corresponding inspection unit 112 reaches the point in its orbit where its vial V and puck 115 have stopped spinning with respect to the vial deck, the contents of the vial continuing to spin. Alternately the reed switch, or switches, 127 may be circumferentially offset in advance of their respective cameras and/or the magnet 256 may be circumferentially offset on the base 23 ahead of the point where each camera is to inspect it corresponding vial, wherein suitable time delay circuitry (not shown) may be provided to compensate for advance actuation of such reed switch 127 due to such offset or offsets. Tripping of a given reed switch 127, either directly or through such a delay unit, is preferably used to permit video signals from its camera to reach the separator and processor units 246 and 247 only during the inspection segment of the orbit of the corresponding vial, i.e., when the vial, but not its contents, have ceased spinning. Conveniently, the camera video is applied to the separator-processor then for a moment (e.g. 400 msec) sufficient for determination by the processor of whether to accept or reject such vial. Tripping of reed switch 127 may thus apply the camera video to the separator-processor in any convenient manner, as through suitable switching indicated at 520 with respect to a single camera in FIG. 12, or alternatively as shown with respect to a single camera in FIG. 13 or multiple cameras in FIGS. 17 and 18.

OPERATION—FIGS. 1–11

While the above description makes apparent the operation of the apparatus, same is summarized below.

Figure 6:
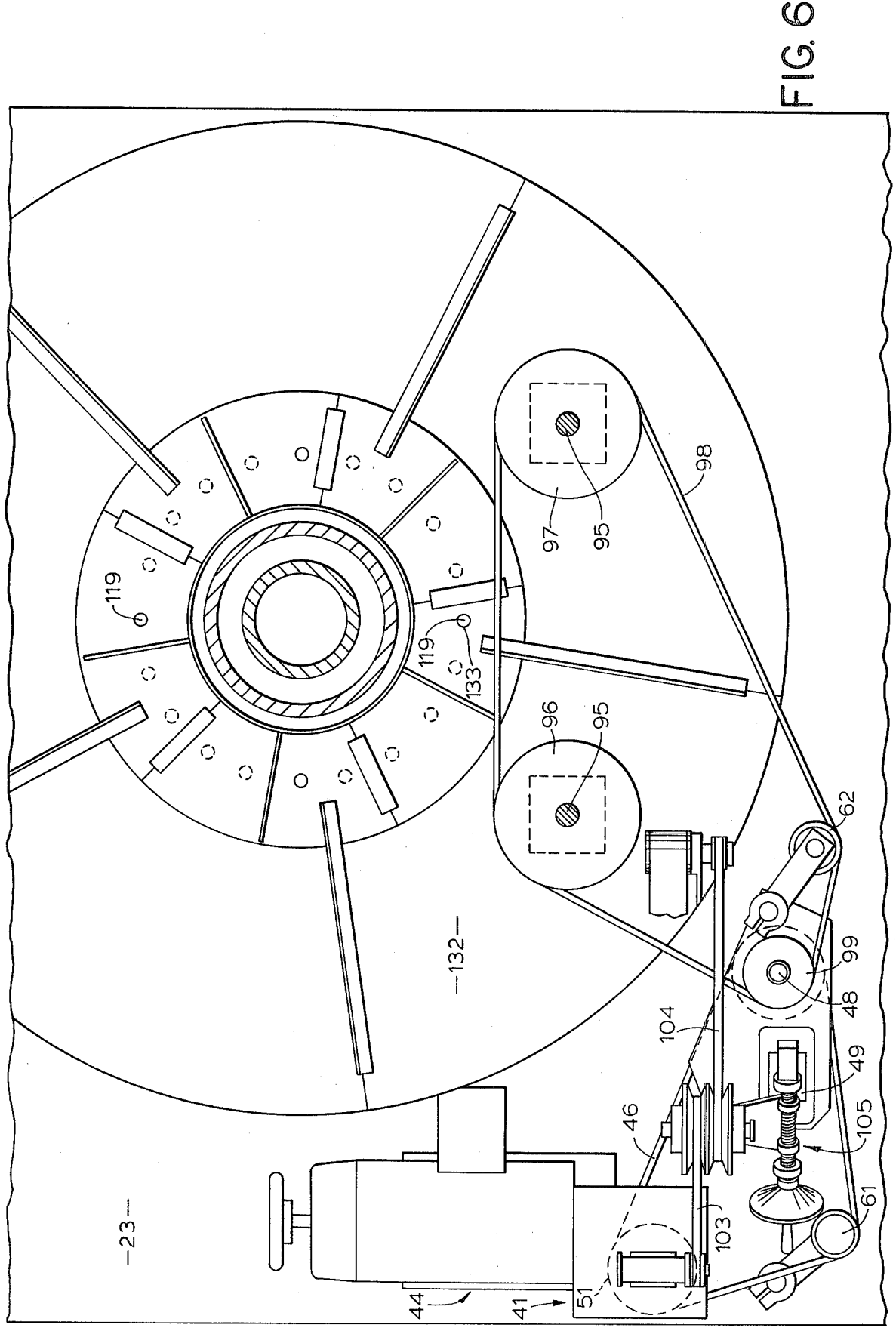
FIG. 6 is an enlarged sectional view substantially taken on the line VI—VI of FIG. 2.

In normal operation, the shell 33, with vial deck 73, light source deck 130, drip shield 132, and camera deck 147 are rotated continuously at a selected speed by the rotational drive system 41. Accordingly, the inspection units 112 (FIG. 4) whose components are carried by such decks, and the circuitry units 246 and 247 all correspondingly rotate. The star wheels 83 and 84 are positively rotated in synchronism with the vial deck and inspection units as indicated in FIGS. 5 and 6. The effective radius of the vial orbit is the same for the star wheels and vial deck and the star wheel speeds are held the same as the vial deck with the angular orientation of the star wheels adjusted such that the vial receiving notches 87 (FIG. 3) of the star wheels repetitively pass over and momentarily align with the same puck 115 of the vial deck 173 once per orbit, or complete rotation, thereof. Driving the vial deck 73 and star wheels in parallel, via positive drive loops 47 and 98, rather than in series minimizes timing error due to any chain, belt, etc. stretch after extended use.

Figure 3:
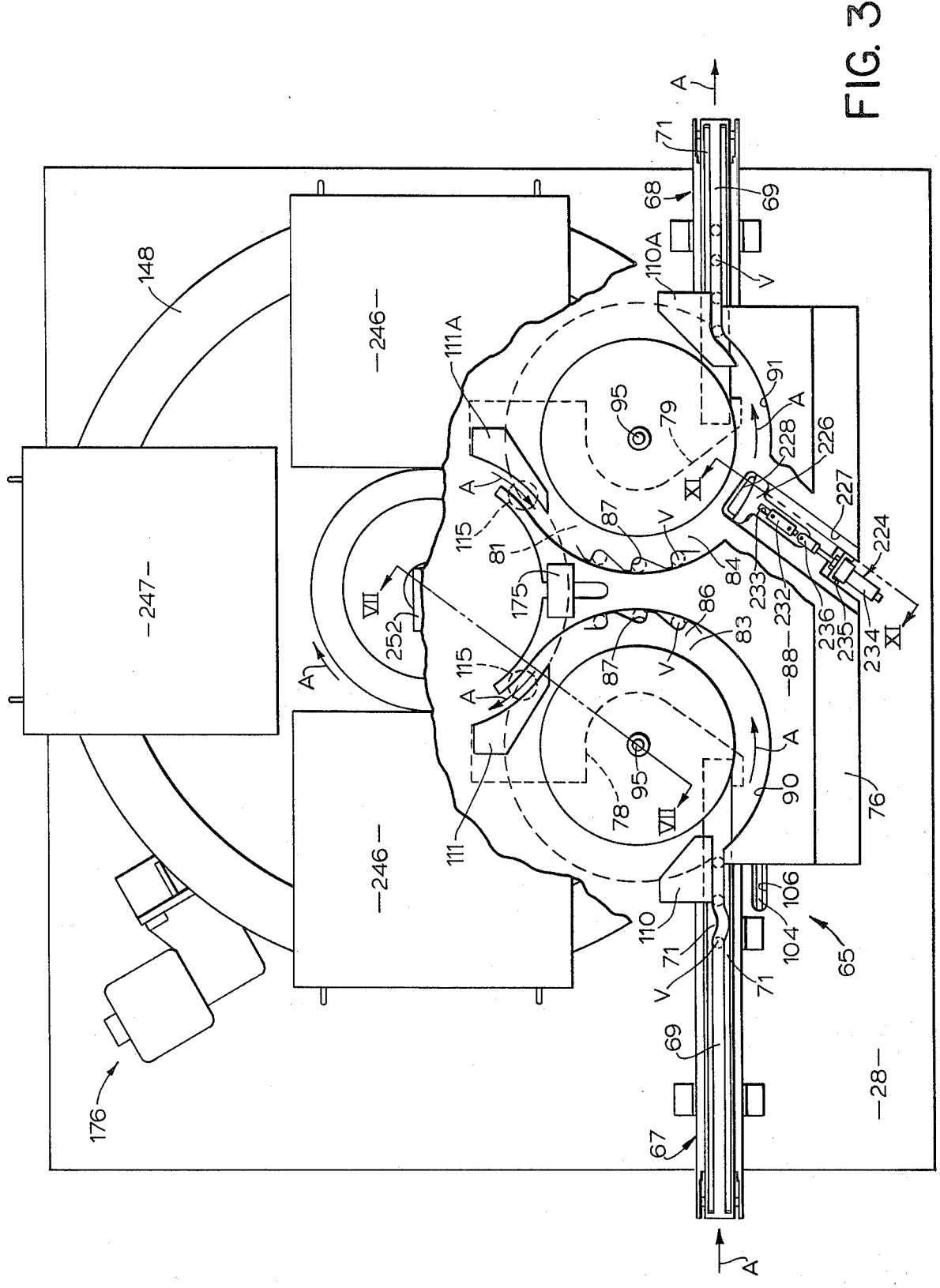
FIG. 3 is a top view of the FIG. 1 machine partially broken away substantially in accord with cutting line III—III of FIG. 2 to show the path of vial travel through the star wheels and further partially broken to show the vial reject mechanism.

The vial input and output conveyors 67 and 68, in contrast, are preferably driven at a somewhat higher vial transfer speed (e.g., 10% faster), preferably from the same drive means 41 and through a suitable speed adjuster, as at 105. Thus, input conveyor 67, which is preferably filled with vials from any conventional source, not shown, can readily feed vials V to the infeed star wheel 83 fast enough to keep the star wheel filled with vials. Similarly, overspeeding output conveyor 68 readily removes all vials V presented to it by the outfeed star wheel 84. In FIG. 3, the arrows A indicate the substantially sinuous path followed by a vial V (particularly a nonrejected vial) through the apparatus.

Vials V fed rightwardly (FIG. 3) atop input conveyor 67 pass one at a time into the orbit of successively presented teeth 86 of the infeed star wheel 83 and are slid thereby off the input conveyor and onto and along vial plate 76, being constrained to orbit with the infeed star wheel by the flanking edge of the side opening notch 90 in the platelike central vial guide 88. The infeed star wheel slides successive vials V onto successively presented pucks 115 of the rotating vial deck 73. The vial being transferred to the rotating vial deck 73 passes beneath the cam member 171 (FIGS. 1 and 2) located in the front sector of the machine. The chuck 154 of each vial clamp assembly 126 (FIGS. 2, 4 and 7) (which is coaxial with its corresponding puck 115) is maintained elevated by support of its cam follower roller 116 on the upper edge of the cam member 171 as such puck 115 and vial clamp assembly 126 rotate through the front segment of the orbit toward the infeed star wheel 83. Thus as a vial V slides from the infeed star wheel onto a given orbiting puck 115, the camming surface of cam member 171 soon begins to drop the vial clamp assembly 126 such that the chuck 164 descends upon the upper end of the vial V to hold same firmly against the puck 115 while assuring coaxiality therebetween by laterally shifting the vial V if necessary.

The thus clamped vial V orbits with its corresponding inspection unit 112 (including clamp assembly 126 and puck 115, beyond the cam member 171, to the adjacent vial spin segment of the vial deck orbit, as defined by the inner reach (as shown in broken lines in FIG. 8) of the puck spin belt 187. Such inner reach of spin belt 187 is continuously rotated, here by the vial spin unit generally indicated at 176 (FIG. 8), preferably at a speed which is adjustable (as by adjustable ratio device 193) to optimize spin speed for the particular vial content in a given run. The inner reach of spin belt 187 frictionally engages the spin and brake pulley 116 of one or more opposed inspection units 112 thereby spinning the vial V carried by a given puck 115 with respect to the orbiting vial deck 73. The inner reach of spin belt 187 is shown at 187' in FIG. 7 for convenience in illustrating its preferred engagement with the spin and brake pulley 116, it being understood that the spin belt 187 is spaced well behind the cutting plane of FIG. 7. Spin belt 187 may orbit in either direction (clockwise or counterclockwise) but clockwise orbiting coacts with clockwise orbiting of the vial deck 73 for somewhat increased spin speed for a given spin belt orbit speed. Vial spin speeds of 500–2000 RPM are typical.

Spinning of the vial V in this manner spins the contents thereof as well and as the vial V orbits with the vial deck 73 past the spin sector (defined by spin belt 187), vial spin is to be stopped, the contents of the vial, including any particles, being allowed to continue to spin, or swirl. In the preferred embodiment shown, the brake unit at 177 follows the spin unit 176 and drives its brake belt 217 in synchronism with orbiting of the vial deck 73 such that the inner reach 219 of the brake belt moves at the same lineal speed as the corresponding portion of the vial deck 73 and by engaging the periphery of the spin and brake pulley 116 halts the spinning motion of pulley 116 and therewith puck 115 and associated vial V, such that the vial V continues to orbit with the vial deck 73 but no longer spins with respect thereto. The liquid contents of the vial V, however, continue to spin and hence are in swirling motion with respect to both the vial V and vial deck 73 as the latter orbits beyond the braking segment of the orbit defined in FIG. 8 by brake belt reach 219.

Thus, the orbiting vial, its contents swirling, is now in condition for inspection and the vial passes into the inspection segment of its orbit with vial deck 73.

During the operation of the machine, the light source 118 and camera 121 at each inspection station 112 are preferably continuously energized throughout each orbit thereof and monitor 241 is preferably also continuously "on". However, the video output of each camera, to the corresponding separator-processor unit 246, 247, and to the monitor 241, is switched and hence is used only during the inspection segment of the orbit of each inspection unit 112. Accordingly, as a given inspection unit 112 leaves the braking segment (here defined by brake belt reach 219 (FIG. 8) the video output of the corresponding camera will be switched automatically to the corresponding separator-processor 246, 247 and to the monitor 241 in delayed or preferably direct response to tripping of the one of the reed switches 127 assigned to that inspection unit 112, and due to movement of such reed switch 127 past the fixed magnet 256. If desired, timing means can be provided to subsequently disconnect the video of that camera from the processor and monitor. On the other hand, tripping of the reed switch assigned to a subsequently appearing one of the inspection units 112 may be used not only to connect its video signal to the monitor and/or a given separator-processor unit 246, 247, but may also be used to disconnect the first mentioned camera's video therefrom. Particularly, the star wheels and vial deck may rotate at 15 rpm and, in the embodiment disclosed, up to 20 inspection units 112 may be spaced circumferentially around the rotating portion of the machine, permitting (with all 20 inspection locations filled) a vial flow rate of 300 per minute. The 15 rpm rotation rate corresponds to 4 seconds per rotation, such that each vial is present on the vial table 73 for about three-quarters of a rotation or about 3 seconds. Time sharing of two separator-processor units 246, 247 by twenty cameras (each separator-processor unit 246, 247 thus handling video for ten vials in sequence per rotation of vial deck 73) permits, in this example, application of camera video for a given vial to the corresponding separator-processor unit for up to about 400 msec, corresponding to 1/10 or about 36° of the vial deck orbit. Such gives adequate time for the circuitry 246, 247 to determine whether or not the given vial has sufficient particle content as to require its rejection.

After the given inspection unit 112 has passed through the inspection segment of its orbit, its cam follower roller 161 engages the input end of cam member 171 and as it moves circumferentially therealong is lifted and thereby lifts the chuck member 164 upward out of engagement with the vial V (FIGS. 2 and 8). As this occurs, the vial deck 73 orbits such vial V into the channel between the platelike central vial guide 88 and outfeeds transfer guide 111A (FIG. 3) and the adjacent tooth of the outfeed star wheel 84 slides the vial off the vial deck 73 and once again along the stationary vial plate 76 toward the reject unit 224. If the vial V is to be rejected (for excessive particle content) the slidable trapdoor 226 (FIGS. 3 and 11) of the reject unit will be open as the vial attempts to move laterally through the reject unit area and, accordingly, the rejected vial will drop through opening 228 into the reject hopper 229. To this end, the trapdoor cylinder 234 (and if desired the blow off nozzle 236) are appropriately delay actuated by the determination of a given processor 247 that the vial V in question has excessive particle content.

On the other hand, where the given vial V is acceptable, the trapdoor 226 remains closed over the reject opening 228 and the outfeed star wheel as it rotates slides such vial V across the closed trapdoor and further along the vial plate 76 into the gap between guide 110A and guide plate edge 91 and thus onto the surface of outfeed conveyor 68 for rightward (FIG. 3) transfer to any desired destination not shown.

A succession of vials V may thus be passed through the apparatus each in the manner above-described.

The apparatus 20 is readily adapted to handling of vials, bottles or the like, of a different size, i.e. of different diameter and/or height. To convert to a different vial diameter, the star wheels 83 and 84, fixed guides 110, 88, 111, 111A and 110A and chuck 164 are replaced by similar members sufficiently differently sized to accommodate the changed vial diameter. Similarly, the guide spacing for the input and output conveyors 67 and 68 is correspondingly changed. To accommodate a different height vial, a new chuck member 164, of appropriate length, is substituted. Readily accommodated differences in vial height and diameter are indicated at V and V' in FIG. 7. Typical vial sizes range from 1 to 100 cc, for example.

Shifting a vial from the infeed star wheel to the vial deck without a change in speed or sharp change in direction minimizes mechanical shock to the vial to advantageously avoid formation of bubbles in the liquid within the vial prior to inspection. Bubbles in a viscous liquid may persist for a long time, and if present at inspection might be erroneously detected as impermissible particles, thus resulting in a false rejection of the vial. Also to avoid bubble formation, the vial spin speed may be reduced as at 193 for a run of vials containing such a viscous liquid.

During the inspection segment of its orbit, each vial V is held very rigidly in fixed relation to its corresponding camera. The apparatus thus is capable of detecting very small particles, as small as 50 microns, despite the high (e.g. 300 per minute) vial flow rate through the apparatus.

DETAILED DESCRIPTION—CIRCUITRY

FIG. 12 discloses in block diagram form the basic inspection circuitry 402 associated with the inspection apparatus 20 above-described. For simplicity, only the major signal paths between circuit blocks are shown and connection for only a single camera 121 is shown.

Since the vials V inspected are taller than wide, better use is made of the rectangular television field with the cameras and monitor tipped 90° onto their sides, so their "horizontal", or scan line, direction is here oriented up and down. As to camera and monitor scanning fields and the FIGS. 12-18 circuitry the terms "horizontal" and "vertical" will refer, respectively, to the direction along the scan line and the direction between scan lines.

Each camera 121 is preferably a low persistence, black and white closed circuit television (CCTV) camera particularly of silicon diode matrix type, referred to as a Tivicon. Such a camera is advantageous in this invention due to its ability to rapidly drop its video output when a viewed light source shuts off (low persistence as contrasted to a conventional lead oxide vidicon) and its high efficiency in converting incandescent light into a video signal (e.g. 17 times better than a conventional lead oxide vidicon).

The monitor 241, each camera 121, the processor unit 247 and the separation unit 246, are synchronized in operation by connection to vertical and horizontal sync lines 404 and 405 from any convenient source, here from suitable circuitry provided within the separation unit 246. The scanning beams of cameras 121 and monitor 241 are thus synchronized with each other and with operations carried out by units 246 and 247. Raw camera video on line 406, as would result from inspection by a given camera of the swirling contents of a vial V, is applied to separation unit 246 which in turn separates and enhances that portion of the video corresponding to viewed elements moving with respect to the camera, i.e., the swirling particles in the vial, while omitting video portions not of interest, i.e., corresponding to viewed elements fixed with respect to the camera such as the vial itself or other substantially fixed visual matter adjacent the vial. The thus separated video is applied through lines 407 (labelled SEP video) to the processing unit 247.

Processing unit 247 includes several serially arranged circuits indicated as a window circuit 409, a horizontal sizer circuit 410 with an associated clock circuit 411, a vertical sizer circuit 412, and a frame counter circuit 413 arranged to actuate vial rejection unit 224. Also, the horizontal sizer circuit provides signals to monitor 241 for display, as at 531.

Figure 13:
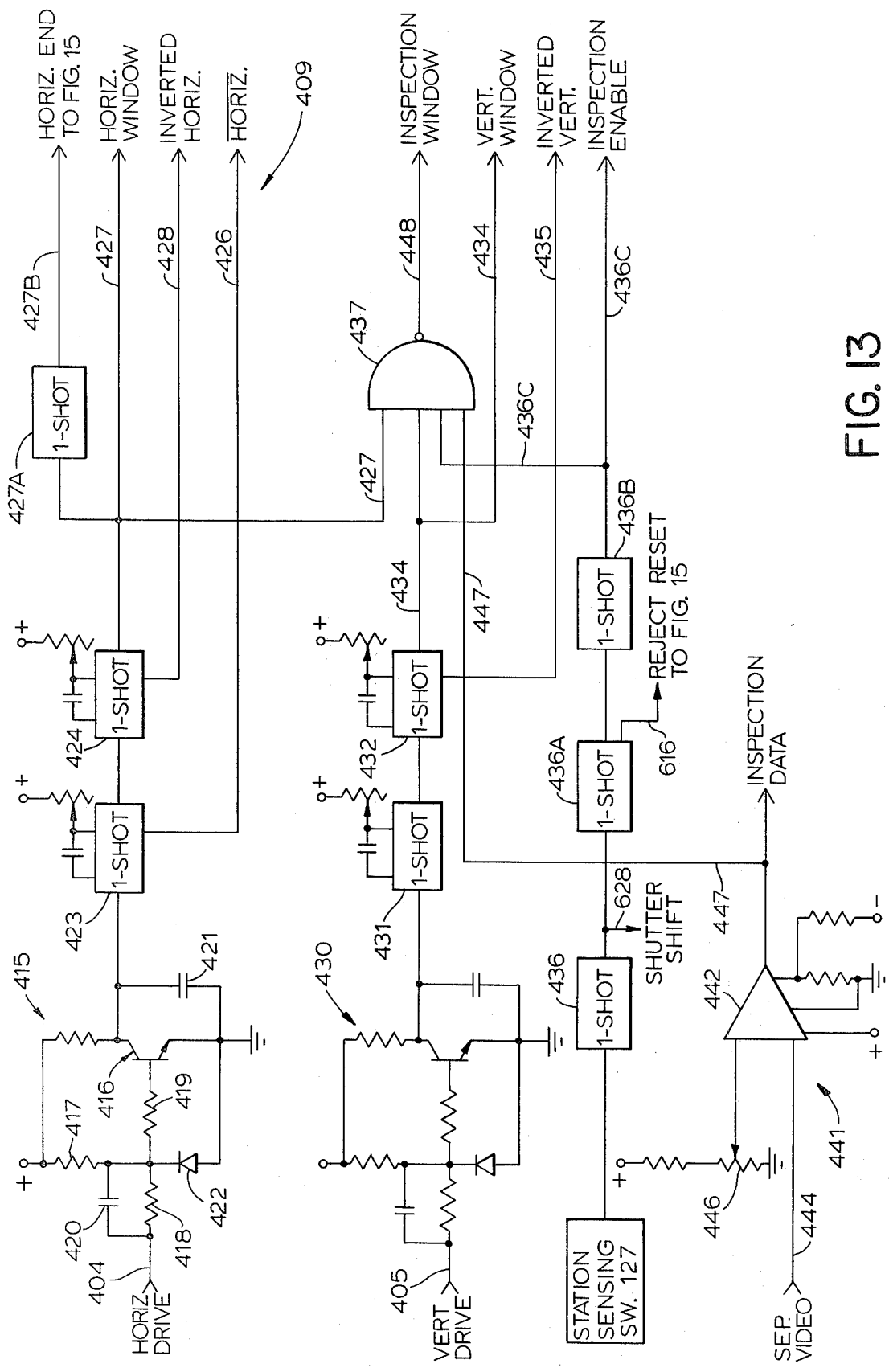
FIG. 13 is a circuit diagram of the window circuit of the FIG. 12 processor.

FIGS. 13-15 set forth the aforementioned circuits 409-413 of processor unit 247 in more detail.

In FIG. 13, the horizontal sync, or drive, signal on line 405 is supplied through a transistor level circuit 415, comprising a transistor 416, associated resistors 417 through 419, capacitors 420 and 421 and diode 422, which translates the incoming video sync signal to a polarity and voltage level appropriate to TTL logic later encountered in the processor unit 247. Basically, level circuit 415 converts the negative going pulse edges of the video sync signals to positive going spikes of desired level suitable for TTL logic.

The horizontal sync output from level circuit 415 is applied to series one-shot multivibrators 423 and 424. The oneshots 423 and 424 determine the edges, or beginning and end in a scan line, of an active window in the camera field. The TTL horizontal sync signal fires the one-shot 423 which times a delay corresponding to the initial portion of the scan line, before the active window is reached. Upon timing out, one-shot 423 marks the beginning of the active window by firing one-shot 424 and by providing a pulse on horizontal line 426.

One-shot 424 then times a delay interval corresponding to the horizontal width of the window and for the duration of this delay interval provides a horizontal window pulse on line 427 and an inverted horizontal pulse on line 428. The end of such delay ends the window portion of that horizontal scan line and the pulses on lines 427 and 428, but causes a further one-shot to produce a brief horizontal end pulse on a line 427B.

The vertical sync, or drive, line 405 similarly connects to a series arrangement of interfaced circuit 430 and series oneshots 431 and 432 which preferably are similar to and operate substantially in the manner of interface circuit 415 and one-shots 423 and 424 above-described. Thus, the vertical sync signal at the beginning of a scanning field of the camera 121, suitably converted to TTL format, fires the one-shot 431, which then times an interval corresponding to the one or several horizontal scan lines lacing the window vertically from the beginning of the scanning field. Upon timing out at the vertical start of the window, one-shot 431 fires one-shot 432 for the duration of its time delay provides a vertical window pulse on line 434 and simultaneously provides an inverted vertical impulse on line 435, marking the active window area for the scanning field.

Figure 16:
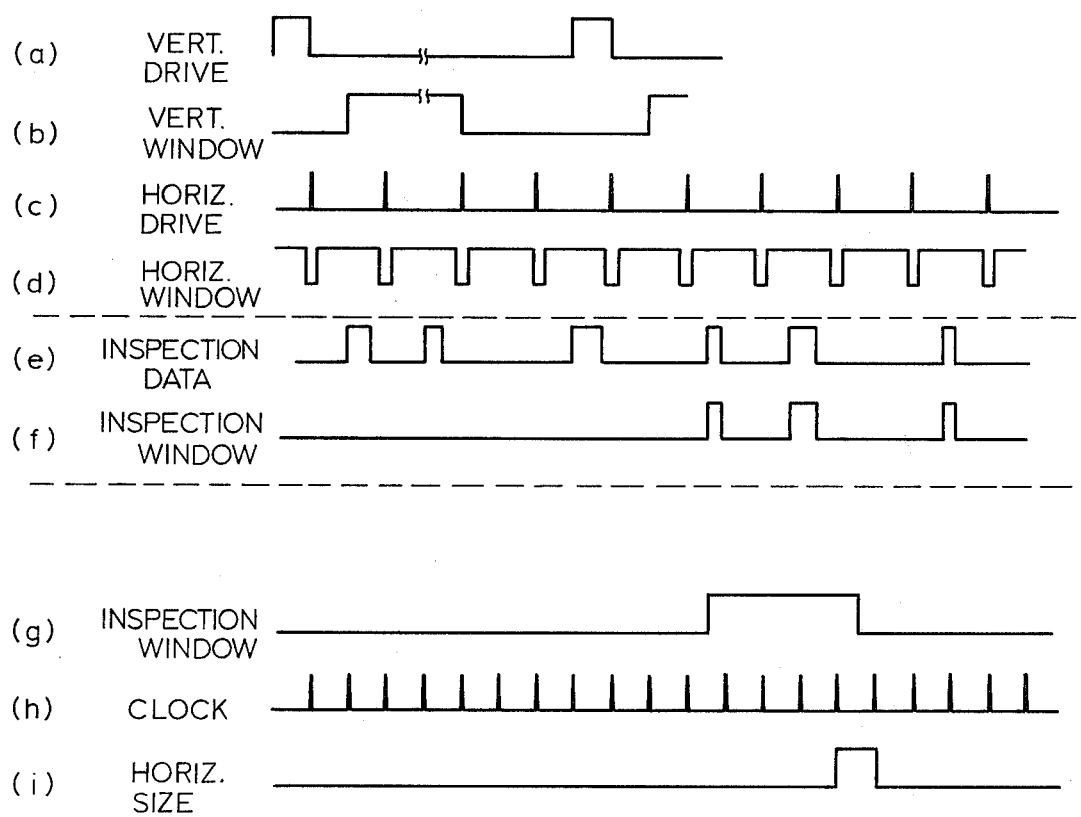
FIG. 16 discloses wave forms for typical signals found in circuitry of the preceding FIGS.

In each scanning field, the plural horizontal window signals on line 427 and the vertical window signal on line 434 enable inputs of a NAND gate 437 while the scanning beam of the camera and monitor lie within a window area indicated at 439 on the screen of monitor 241 in FIG. 12. The vertical and horizontal drive signals and vertical and horizontal window signals above-discussed are shown in FIG. 16 at (a)-(d).

In the embodiment of FIG. 13, to permit operation of the processor only when a camera has moved into the inspection segment of its orbit, the corresponding reed switch 127 is used to trigger a series of one-shot multivibrators 436, 436A and 436B, which time a series of delays. Thus, upon activation of such switch 127, one-shot 436 times, e.g. for 40 nsec, and produces a shutter shift pulse and triggers one-shot 436A. One-shot 436A then times, e.g. for 40 nsec and produces a reject reset pulse and triggers one-shot 436B. One-shot 436B then times an inspection enable interval, e.g. 200 msec, and during that time enables an input line 436C of NAND 437. Accordingly, NAND 437 is thus enabled after the corresponding vial has been spun and stopped and while the liquid contents of the vial continue to swirl.

The window block 409 (FIG. 13) also includes a digitizer circuit 441 comprising a high-gain operational amplifier 442 connected as a level comparator, with one input connected to the video output line (labelled SEP video) 444 of separation unit 246. Basically, the separation unit 246 eliminates from the raw camera video on line 406 those portions representing background and vial structure which are fixed with respect to the camera, but applies to its output line 444 those portions of the video signal dealing with any particles which may be swirling in the liquid in the vial V under inspection.

The unit 246 can thus be said to provide a dynamic grayscale basis wherein the relatively stationary vial V is removed (with other background) from the SEP video. The unit 246 actively provides a high degree of video contrast between fixed and moving objects, substantially boosting the video signal level for moving particles and reducing the video level for the relatively fixed vial and background. Thus, unit 246 can be considered to make the fixed background and vial blacker than black and the moving particles, if any, whiter than white. Application of SEP video to the screen of monitor 241 could thus produce a picture wherein a moving particle P appears as a white dot or blotch on the screen but wherein the vial V containing same is not visible on the monitor screen (through being indicated in broken lines in FIG. 12 for convenient reference).

The other input of level comparator 442 receives a manually adjustable DC reference voltage from a voltage divider 446. Comparator 442 removes any ambiguity from the incoming video by producing only two discreet outputs, which can be characterized as a logic 0 or logic 1, in response to any SEP video input. The comparator 442 further has a relatively fast rise-time and in effect, squares up the incoming SEP video pulses. The comparator 442 thus places the incoming SEP analog video in a form usable by digital circuitry.

Thus, the output of comparator 442 is applied through a line 447 to a remaining input of NAND 437 and comprises a pulse when the camera line of scan crosses the image of a particle in the vial V.

Nand gate 437 produces a logic 0 output in response to all positive inputs, indicating that the camera is in the inspection segment of its orbit and its scanning beam is within the window 439 and such beam is crossing a particle, or flake, such as indicated at P in FIG. 12. The duration of the negative going pulse on the output of NAND gate 437 corresponds to the width of the particle being scanned and appears on inspection window line 448. Typical inspection data and inspection window signals from lines 447 and 448 appear in FIG. 16 at lines (e) and (f).

The horizontal sizer circuit 410 (FIG. 14) comprises a serial input, parallel output shift register 450 (here of four bit capacity). The clock input 451 of shift register 450 is driven by clock 411, which here comprises a timing and control network including resistors 452 and 453, capacitor 454 and inverters 455 and 456, which directly, and through a further inverter 457 alternately actuates the inputs of a flip-flop 458, one output of which drives the clock line 451 at the clock rate.

Thus, the shift register samples the voltage on the inspection window line 448 (through an inverter 459) which causes a particle or flake pulse to be positive going as in FIG. 16 at (f) and (g). Such voltage samples are advanced by the shift register 450 at the clock rate and are applied through the parallel outputs of the shift register to a NAND gate 461. Thus, to actuate NAND 461, the horizontal size of the scanned particle or flake must be above a certain threshold width, here corresponding to the distance traversed by the camera scanning beam in four cycles of the clock 411. Thus, a sufficiently wide flake pulse on line 438 fires the NAND 461, producing a negative going horizontal size pulse on line 462, which when inverted as hereafter discussed appears as the horizontal size pulse at line (i) of FIG. 16. Appearance of such a horizontal size pulse on line 462 suggests that the camera 121 has "seen" a particle of sufficient width to be of interest while scanning the corresponding vial V.

It is convenient to employ conventional closed circuit television sync timing. Accordingly, in the embodiment shown, the horizontal sync pulse occurs every 63.5 usec (a horizontal scan line length of 63.5 usec is employed), a 525 scan line frame of two interlaced approximately 262 scan line fields is employed and other sync pulse characteristics are conventional. The contemplated range of clock frequencies is from about 10 Mhz to about 33 Mhz, i.e. a pulse rate cycle of about 33 to 100 nsec in length, with a 43 nsec clock interval being a suitable example. Such rates are typical performance for TTL logic and provide suitable resolution.

By limiting particle or flake sensing to the central portion of the camera field, i.e. within the window 439, spurious signals unrelated to presence or absence of particles or flakes in the vial are eliminated from the video. Such spurious signals would include the horizontal and vertical signals and any related noise occuring when the camera scanning beam is near the edges of the field. Thus the provision of the active window 439 substantially increases the accuracy and effectiveness of the processor unit 247 and substantially reduces errors in rejection of vials.

It will be noted that the above-mentioned timing provides substantial sensitivity insofar as detectable particle or flake size is concerned. Where, for example, the window 439 covers a substantial portion of the width of the scanning field, and covers substantially the full width of the vial, particles of only one hundredth or so the width of the vial could trigger the horizontal size NAND 461.

It will be apparent that by changing the interval of clock 411 and/or the capacity of register 450 and NAND 461, that the particle width detection threshold can be made larger or smaller.

The horizontal sizer circuit 410 here includes monitor drive circuitry generally indicated at 464, hereafter described.

The vertical sizer circuit 412 (FIG. 15) includes the further series input, parallel output shift register 466 (here a four position register) whose outputs when simultaneously actuated fire a NAND gate 467. A four bit capability has been found sufficient in practice, but if desired the bit capability of the register-NAND gate arrangement can be increased by providing in series with register 466 a further similar register 468, the outputs of which drive the corresponding NAND 469 as here shown.

Where both NANDS 467 and 469 are present, their outputs are applied to the inputs of an inverted input AND gate 470 which when both NANDS 467 and 469 fire in turn fires a NOR gate 471 providing a negative going pulse on a horizontal-vertical (H-V) size line 472. An inverter 473 enables NOR 471. Where the extra register 468 and NAND gate 469 are omitted, gates 470, 471 and 473 can also be omitted and the output of NAND 467 can be directly connected to H-V size line 472.

The flip-flop 475 is capable of being set once in each scan line by appearance of a horizontal size pulse on line 462 and upon being set applies a data bit through a line 467 to the data input of shift register 466. The brief horizontal pulses appearing on line 426 each time a scan line crosses the border into the window area, is applied to the reset terminal of the flip-flop 475 to ready same for a possible incoming horizontal size pulse on that scan across the window area. The brief horizontal end pulse appearing on line 427B as the scan line proceeds beyond the end of the window is applied to the clock input of shift register 466 to shift the data in the register one place. Thus, should a horizontal size pulse occur on four successive scan lines, a logic 1 will appear on each of the four parallel output lines of shift register 466 and fire NAND 467 and such, in the absence of elements 468–470, 471 and 473, provides logic 0 signal on line 472. Such logic signal indicates a disturbance in the field of view of sufficient magnitude as to be of interest, and is termed an H-V size pulse.

Where the second shift register 468 is present, its data and clock inputs 477 and 478 are energized from initial shift register 466 such that the contents of the latter overflow into shift register 468, providing a total register capacity of eight data bits.

Where desired, a fixed width pulse can be produced for each horizontal size pulse. The latter of course are capable of relatively substantial width where relatively wide (substantially greater than the four clock pulses) particles are being scanned. Thus, a fixed width "processed video" pulse can be derived from each variable width horizontal size pulse, as seen in FIG. 15, by coupling the negative going horizontal size pulse on line 462 through an inverter 480 and a series pair of one-shot multivibrators 481 and 482, which provide a square, fixed duration processed video pulse on processed video line 484 for any desired use. In that instance, the horizontal size pulse from line 462 may be applied to the set terminal of flip-flop 475 through such inverter 480 and a NAND gate 483, which serves for isolation.

The frame counter circuit 413 includes a further series input, parallel output shift register 485 whose parallel outputs drive a further NAND gate 486, which when fired provides a logic 0 output on line 487.

The pulse appearing on inverted vertical line 435, when the window area is being scanned, is used to control data input from line 472 into the shift register 485. More particularly, the leading edge of such inverted vertical impulse on line 435 is applied to a one-shot 493, is shaped thereby and is applied to the reset input 494 of a flip-flop 488. The flip-flop 488 then resets before the beginning of the scanning window.

An H-V size pulse on line 472 sets the flip-flop 488, causing such flip-flop to provide an output through line 489 to the data input of shift register 485. The trailing edge of the inverted vertical impulse on line 435, occurring at the end of a scanning of the window area in the field, is shaped by a one-shot 490 then goes as a clock pulse to the shift input 491 of register 485 causing the data therein to shift one place.

Firing of NAND 486 triggers a one-shot 496 connected to provide a "reject" pulse of sufficient length and voltage to actuate suitable counter and display means as at 243 in FIGS. 1 and 15 so as to indicate quantity of acceptances or rejections among vials processed by the apparatus. Such an output from one-shot 496 may also be used to drive suitable alarm means 497, audible and/or visible, to direct the operator's attention to the rejection of a vial. Such an output from one-shot 496 also acts through suitable pressure fluid means P (e.g. a solenoid controlled valve for an air pressure supply) to actuate the blow off and reject cylinder devices 234 and 236 above described with respect to FIG. 11, and thus remove from the stream of vials, that vial which triggered NAND 486 and one-shot 496. Thus, as above described, the disclosed apparatus detects and rejects vials containing objectionally large particles.

However, a sufficiently out of focus camera may fail to cause the above described FIGS. 13–15 circuitry to reject a vial with objectionable particle content. To overcome this possibility, the processor 247 here includes an out-of-focus detector circuit 601 (FIG. 15). Detector 601 is based on recognition that, first, the scene examined by the camera normally contains abundant fine detail, e.g. numerous scratches or motes on the vial, smaller than objectionable particles which if present in the vial would cause rejection thereof, and second, a camera capable of discerning detail at least somewhat finer than the objectionable particles is focused sufficiently to detect such objectionable particles.

In circuit 601 a NAND gate 603 has inputs from the horizontal drive line 404 (FIG. 13), the vertical drive line 405, the inspection enable line 436C, and a digitizer circuit 604. Digitizer 604 is preferably like digitizer circuit 441 of FIG. 13 and hence is shown merely in block form. Digitizer circuit 604, unlike digitizer 441, receives raw camera video, free of sync signals, as from camera video output line 406 of FIG. 12, and converts the continuously varied amplitude analogue video waveform to a nonambiguous two level (logic 0, logic 1) waveform, or pulse train, useable by digital circuitry. During the active scanning (nonretrace) part of the camera field, with the camera in the inspection part of its orbit as indicated by the inspection enable line 436C, the NAND 603 transmits the pulse train, produced by scanning of the camera beam across visually contrasting parts in the scene before it, through a line 606 to the data input of a shift register 608. The parallel outputs (conveniently four as shown) of shift register 608 connect to the inputs of a NAND gate 461A, with inverters 612 and 613 interposed in the outermost (first and fourth) output lines of the NAND 461A. The shift input of register 608 is supplied clock pulses, preferably through line 451 from clock 411 (FIG. 14) to shift data on line 606 serially through shift register 608 at the same shift rate as aforementioned H-size shift register 450. Thus, register 608 samples the "digitized video" on line 606 many times per camera scan line.

To provide a unique (here logic 0) output, the NAND 461A requires the outputs of shift register 608 to read (0, 1, 1, 0). At the clock rate suggested, electronic noise is quite unlikely to generate this register output, since a single electronic noise pulse would normally be substantially narrower (in time or along the scan line) than one, let alone two, clock pulse cycles on line 451. On the other hand, the reading (0, 1, 1, 0) on register 608 would result from a properly focused camera scanning a mote or other visible detail somewhat narrower than the narrowest in-vial particle considered objectionable, which objectionable particle would in this embodiment have a minimum width corresponding to an output at register 450 (or register 608) of (1, 1, 1, 1). Accordingly, the output (0, 1, 1, 0) from register 608, resulting in a unique (here 0) output from NAND 461A, suggests that the then inspecting camera is in good enough focus for proper particle detection and vial rejection by the processor 247.

The focus detector 601 further includes a RS flip-flop 614 coupled at its S input through line 462A to the output of NAND 461A. Flip-flop 614 is reset prior to the period of camera inspection of the vial from the reject reset output line 616 of aforementioned one-shot 436A (FIG. 13). The reset flip-flop 614 carries a logic 1 at its Q output, but upon subsequent setting of the flip-flop 614 by an in focus output from NAND 461A, the Q output of flip-flop 614 switches to a logic 0.

An AND gate 618 has its data input connected to the Q output of flip-flop 614 and further has an enabling input connected to the inspection enable line 436C through a time delay one-shot 619. In response to initiation of the relatively long (here 200 msec) inspection enable signal on line 436C, the one-shot 619 times a delay preferably extending through most of the inspection enable period, and then switches output polarity to provide a positive, or logic 1, enabling pulse of short duration to the enabling input of AND gate 618. if the camera is in focus, flip-flop 614 will have been set by NAND 461A early in the inspection interval and will remain set, applying a logic 0 to the AND gate 618 for the remainder of the inspection period, and the enabling logic 1 from one-shot 619 near the end of the inspection interval will not switch AND gate 618, which continues its normal logic 0 output. On the other hand, if the camera is out of focus, NAND 461A will not have set the flip-flop 614 and the latter stays reset during the inspection interval, keeping a logic 1 on the data input of AND gate 618. Accordingly, the appearance of the logic 1 enabling pulse from one-shot 619 switches AND gate 618 to a logic 1 output indicating an out of focus camera.

This out of focus output of AND gate 618 may be used to trigger a suitable out of focus alarm 621 if desired, but preferably is used to reject the vial viewed by the out of focus camera, to avoid accidental acceptance of an objectionable vial.

To permit rejection of a vial in response to either objectionable particle contamination or a nonfocused condition of the associated camera, the outputs of one-shot 496 and AND gate 618 are applied to a NOR gate 623 which, in response to a reject signal from either source, will set a flip-flop 625 to its reject condition.

Prior to each inspection interval (passage of each camera-vial pair through the inspection segment of the machine orbit), the flip-flop 625 is reset (along with flip-flop 614 above mentioned) here by the reject reset pulse on line 616 from one-shot 436A of FIG. 13, such that the reset and non-reject conditions of the flip-flop 625 coincide. Setting of flip-flop 625 results in its applying a reject output, sometime in the inspection interval for a given vial, through line 626 to the D input of a D-type flip-flop 627. The output state of the D flip-flop 627 does not of course change as yet, providing time for the offending vial to leave the inspection segment of its orbit, and proceed with the outfeed star wheel 84 (FIG. 3) to the vial rejection unit 224. When the offending vial has had time to reach the vial rejection unit 224, a shutter shift pulse is supplied at line 628 to the clock input of D flip-flop 627, clocking thereinto the reject signal on its input line 626. Thus, the D flip-flop 627 changes output state and applies a reject signal to the pressure fluid source P for causing the reject cylinder 234 (FIG. 11), and if desired the blow off nozzle 236, to route the offending vial to the reject hopper 229. The shutter shift pulse on line 628 is, in the embodiment shown, supplied by one-shot 436 (FIG. 13) immediately before the reject reset pulse on line 616 resets flip-flops 614 and 625. In this way, a reject output from flip-flop 625 will be passed by D flip-flop 627 to trigger the reject unit 224, before flip-flop 614 and 625 are reset in anticipation of inspecting another vial.

Where, as in the embodiment of FIG. 3, the distance of travel of a vial, from the inspection segment of its orbit to the outfeed star wheel location over the reject unit 224, corresponds to substantially one-half rotation of vial deck 73, the shutter shift pulse on line 628 will be wanted about half a vial deck rotation after initiating of the inspection enable signal on line 436C for the vial to be rejected. This would be accomplished by actuation of the station sensing switching 127 twice per rotation of the vial deck if the shutter shift pulse is to be obtained from one-shot 436 as shown in FIG. 15, such that the use of one-shot 436 as a shutter shift pulse source for line 628 would provide proper timing in a two camera machine. On the other hand, the shutter shift pulse on line 628 may be provided from any convenient source, for example from simple time delay means, such as a one-shot (not shown), having an approximately one-half rotation delay interval initiated, for example, by the output of station switch 127 or one-shot 436A or 436B.

The monitor drive circuitry 464 of FIG. 14 permits display on the monitor of operating characteristics of the apparatus including display of the read window 439 and one or more desired signals relating to or derived from detection of particles or flakes in the vial under inspection. The monitor 241 (FIG. 12) is a color television unit set up for CCTV use. Preferred is a "Trinitron" model manufactured by Sony of Japan.

The color monitor 241 permits display of several different kinds of information on the monitor screen simultaneously yet distinguishably by using different colors, e.g. blue, green and red, for different kinds of information. The operator thus can more reliably and quickly follow and react to a rapidly changing and/or more complex information display than with a mere black and white monitor.

In the embodiment shown, the black and white row video signal from the camera 12 (FIG. 12) is fed through video line 406 to the "Y", or picture luminance, input of the monitor 241. The result here is a monitor display, in shades of green, of the scene viewed by the camera 121, usually the corresponding vial in its view (which for illustration is indicated in dotted lines at V in FIG. 12).

To provide a further portion of the monitor display, the monitor drive circuit 464 (FIG. 14) includes a NOR gate 501 having inputs connected to the horizontal window and vertical window lines 427 and 434 of FIG. 13, such that when the scanning beam of the camera is outside read window 439, logic 0's on line 427 and 434 provide a logic 1 output from NAND gate 501 on a line 502 which connects in any conventional manner to one of the color gun circuits of the monitor 241, here for example the blue color gun circuit. In consequence, that portion of the monitor screen inside read window 439 is maintained green in color, in contrast with the blue display outside the window area.

SEP video is here applied through an inverter 504, an inverted input OR gate 509 and an inverter 511 to the red gun circuit input line of the monitor 241. Thus, an SEP video pulse, e.g. produced when the camera beam scans a particle in the vial, in turn produces a red spot P on the monitor screen. Typically, red spots appear here and there on the monitor screen as a vial is scanned by its camera. Also, white spots may appear, due to the raw video image fed to the monitor luminance input at 406, and in a conventional color monitor a red spot may be slightly displaced from a corresponding white spot.

To forceably warn the operator that there is a substantial probability that an unacceptably large particle exists in a vial under inspection, an appropriate signal, such as the H-V size signal, or preferably (as shown in the present embodiment) the H size signal is coupled through a branch of line 462, to a one-shot multivibrator 507 (FIG. 14). When energized by such an H size pulse, the one-shot 507 produces a relatively long output pulse (for example corresponding to about three scan lines of the camera), which is applied to the remaining input of OR gate 509.

The inverted input OR gate 509 thus passes not only the SEP video pulses but also such an elongate pulse from one-shot 507 for actuating through the inverter 511 the red gun circuit input line 512 of the monitor 241. Thus, an H size pulse, produced when a scan line is crossing a particle of sufficient width, produces through one-shot 507 and gate 509 a highly visible red bar B (FIG. 12) on the monitor screen, of full line width and several line thickness and covering the corresponding red spot P, to alert the operator. For a vial having a given particle mix, the monitor will display a changing pattern of red dots P with perhaps an occasional red bar B.

The inspection circuitry has been discussed above with respect to a single camera for convenience. However, the present invention extends to multiple cameras and may be operated with partial camera capacity (e.g. four cameras) and a single separation unit 246 and processor unit 247 as in FIG. 17 or with a full complement of cameras (e.g. 20) and a pair of separation units 246 and processor units 247 as in FIG. 18.

Figure 17:
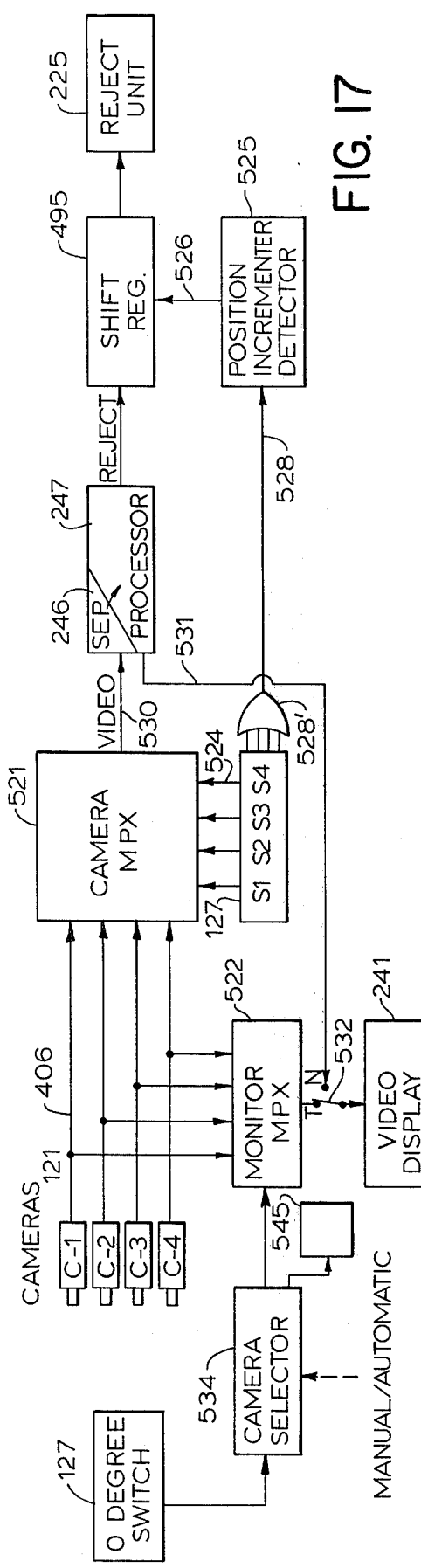
FIG. 17 is a block diagram of the inspection circuitry for a system wherein multiple cameras (four being illustrated) share a single separator-processor and FIG. 17A shows a part thereof.

Processor 247 acts on video information from a given camera in less than one rotation of the apparatus and accordingly a single separation processor unit 246, 247 can be time shared by several cameras as schematically indicated in FIG. 17. The parallel video output lines 406 of several cameras 121 (respectively at C1, C2, etc.) are applied to a camera multiplex circuit 521 and to a monitor multiplex circuit 522.

As above discussed, each of the cameras 121 has a respective reed switch 127 in a predetermined circumferential location with respect thereto. Here the reed switches are on the light source deck 130 and are tripped in sequence by the fixed magnet 256 as the cameras rotate. Preferably a given switch 127 is tripped as its camera rotates into inspection position, to view the swirling contents of its associated vial. Each switch 127 thus acts as a position sensor for its associated camera. The several switches 127 (schematically indicated at S1, S2, etc. in FIG. 17) are thus tripped in sequence, as the cameras and vials rotate, and each, in sequence, provides a pulse on the corresponding one of lines 524 to the camera multiplexer 521.

The camera multiplexer 521 may be a conventional switching circuit of convenient type capable of coupling the video line 406 of each of the cameras C1, C2, etc. in sequence to a video line 530 leading to the separator-processor circuitry 246, 247, in response to corresponding camera position switch signals appearing sequentially on the several lines 524. For example, tripping of camera position switch S2 causes multiplexer 521 to couple the video output of camera C2 to line 530, holding same there until the next switch S3 is tripped which causes multiplexer 521 to disconnect the video from camera C2 from line 530 and instead substitute the video from camera C3. The sequence continues thus as the cameras and vials rotate in normal operation of the machine.

When the processor circuit 247 determines that a given vial, then under inspection by its corresponding camera, is to be rejected, the shift register 495 delays the reject signal going to the reject apparatus 224 long enough for the offending vial to pass from the rotating vial deck 73 into the outfeed star wheel 84 and reach the reject mechanism 224 as the latter is being actuated. The shift register 495 may conveniently be incremented by the sequential tripping of the camera position switches 127. As schematically indicated in FIG. 17, therefore, any suitable pulse source 525, here labeled position increment detector, transfers a fixed number (1 or more) of pulses to the shift input 526 of shift register 495 each time one of the camera position switches 127 is tripped. The detector 525 senses tripping of switches 127 in any convenient manner, as schematically indicated by the line 528 and OR function gate 528'. Accordingly, the "length" of the shift register 495 and number of pulses applied thereto from line 526 can readily be made to correspond to the time required for the defective vial to reach the reject mechanism 224.

The video from the plural cameras 121 is normally fed to the monitor 241 for display in the same sequence as to the separator-processor circuitry 246, 247, for simultaneous display and processing of the video from each camera in sequence. The system operator should also be able to instead manually control, under certain circumstances, which camera has its video displayed on the monitor. Such manual selection is useful in initial set-up of the apparatus and where the operator may notice an unusual monitor display suggestive of a malfunction in one of the rotating inspection stations 112 (e.g., of the light source or camera thereof) wherein the cameras can be manually selected for display on the monitor one at a time until the offending station is located. Once the offending inspection station 112 is located, the operator can insert a suitable plug or blocking device (not shown) into the corresponding vial notch on the infeed star wheel 83. Since the infeed star wheel and vial deck have the same rotative speed and number of vial locations, the mentioned plug in the infeed star wheel precludes feeding of vials to the offending rotating inspection unit 112. Such permits inspection of vials by remaining stations 112 of the apparatus until it becomes convenient to shut down the apparatus to correct the malfunctioning inspection unit 112.

Thus, for normal operation, the particular processor outputs discussed above or to lines 502 and 512 in FIG. 14 are taken from separator-processor 246, 247 and applied to monitor 241 through a path 531 and a multipole normal-test switch 532, so that the camera output being processed simultaneously gives a display on the monitor. On the other hand, when the operator wishes to otherwise control the display for a camera or cameras, the camera video from lines 406 can be taken directly through the monitor multiplexer 522 and applied to the test position of switch 532 to the monitor 241. Thus, the monitor multiplexer may be a conventional switching circuit of any convenient type capable of coupling a selecting one of video lines 406 to the monitor 241 with switch 532 in test position. Switching of monitor multiplexer 522 may be controlled by a suitable control 534, here labeled camera selector, which may be operated manually or automatically. In the latter mode, the camera selector 534 is synchronized with rotation of the inspection units 112 (hence cameras 121) by a once-per-rotation tripping of a zero degree switch 127 to display the video output of a selected camera (or cameras) as the latter rotates through the vial inspection segment of its rotation. The zero degree switch can be a preselected one of the aforementioned camera position switches 127 (e.g. switch S1), or a separate but simultaneously operated switch, or a separate switch located as desired on the rotating part of the apparatus for triggering by a suitable fixed magnet such as magnet 256.

Figure 18:
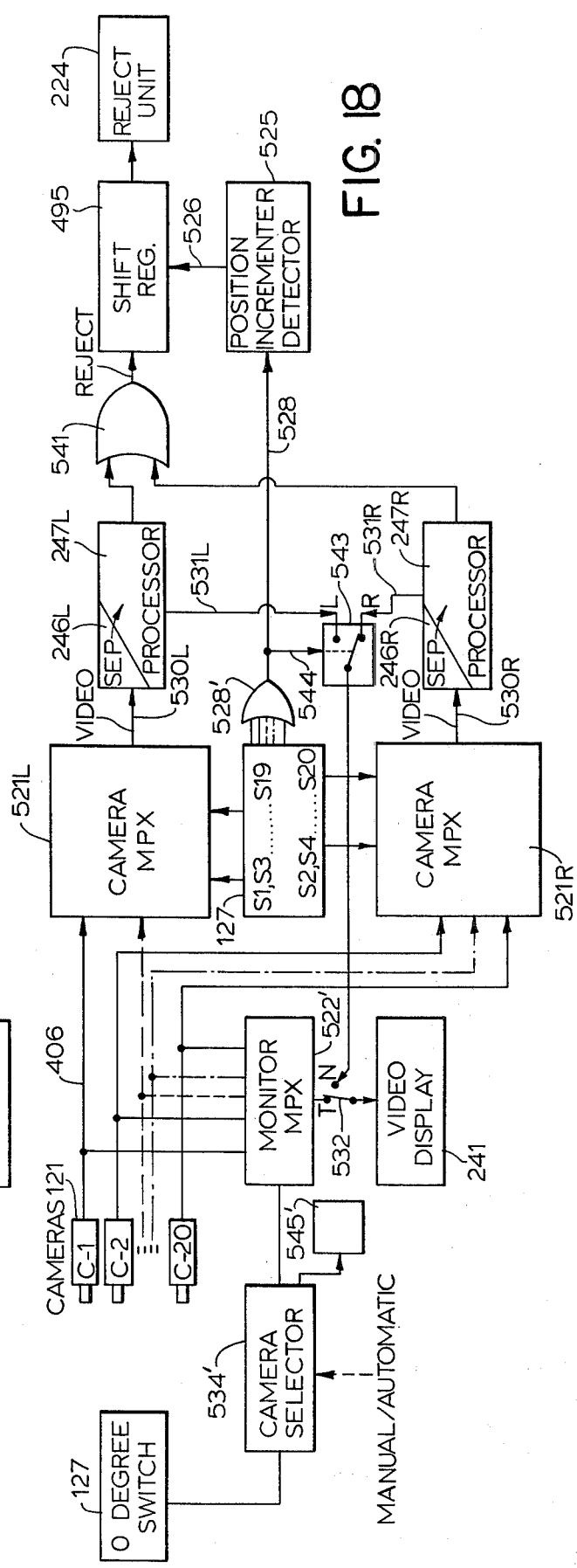
FIG. 18 is a block diagram of the inspection circuitry for a system where a larger number of cameras (twenty being shown) time share a pair of separator-processors and a common monitor.

The FIG. 18 schematic circuit is similar to that of FIG. 17 but is for controlling processing and display of video from more cameras than can be handled by a single separation-processor circuit 246, 247 at the desired rotational rate of the apparatus. For example, 20 cameras may be arranged circumferentially in series (C1, C2 ... C20) on the camera deck 147. In FIG. 18 alternate cameras C1, C3 ... C19 sequentially drive a first separation-processor unit 246L, 247L through a first camera multiplexer 521L, and the remaining cameras C2, C4 ... C20 sequentially drive a second separation-processor unit 246R, 247R through a second camera multiplexer 521R. Analogous to FIG. 17, switches 127 (ones being indicated schematically at S1, S2, S3 .. . S20) correspond to and rotate with corresponding ones (C1, C2 ... C20) of the cameras 121. Thus, sequential tripping of position switches S1, S3 ... S19 sequences the vial inspection video of cameras C1, C3 ... C19 through camera multiplex switching 521L and tripping of position switches S2, S4 ... S20 sequences the vial inspection video from cameras C2, C4 ... C20 through multiplexer 521R. Reject signals from the two processors 247L and 247R can occur only in the sequence in which cameras C1, C2, etc., rotate past the inspection portion of the apparatus. Thus, the outputs of such processors applied through an OR gate 541 to the aforementioned shift register 495 cause rejection of defective vials as in FIG. 17.

In normal ongoing operation, as in FIG. 17, the vial inspection video from the cameras 121 may be displayed in sequence (C1, C2, C3 ... C20) on the monitor 224, by any conventional means. In the example schematically shown in FIG. 18, signals from the processor output paths 531L and 531R are applied to a multipole alternating switch 543 synchronized with application of each camera's vial inspection video to its separation-processor, e.g. as schematically indicated by the OR connection 544, 528' to camera position switches S1, S2 ... S20. Thus, with switch 532 in its "N" (normal) position, the monitor displays the SEP video, bars B, etc. in sequence (D1, C2 ... C20) synchronized with processing of each camera by the separator-processors, as in FIG. 17. On the other hand, the operator can control which camera has its video displayed on the monitor 241, and this may be done substantially as discussed above respecting FIG. 17. Monitor multiplexer 522' and camera selector 534' may be similar to but larger in capacity (e.g. for 20 rather than four cameras) than units 522 and 534 of FIG. 17. Again the operator may simply manually select a camera (e.g. C3) for continuous display or call for several cameras in automatic sequence. Preferably as in FIG. 17, the camera selector comprises a timer (not shown) synchronized with camera rotation by the zero degree switch 127 for keeping track of when in the time continuum each camera C1, C2 ... C20 is in the vial inspection segment of its orbit, and thereby readily actuable by the operator to cause monitor multiplexer to automatically pass video for a selected pattern of cameras, e.g.: all cameras, all odd (C1, C3 ...) cameras, all even (C2, C4 ...) cameras, selected cameras (e.g., C6, C8 or C15, C16, C17), etc. Preferably, conventional indicator lamps or digital indicators 545, 545' associated with camera selectors 534, 534' inform the operator which camera or camera group is inspecting at any given instant and/or has its video displayed on the monitor.

While application of specific signals to the monitor 241 has been discussed above, and shown in the drawings, for illustration, suitable wiring and switching may be provided to enable the system operator to display on the monitor any signals existing in the apparatus (e.g. from cameras 121 to reject means 224) or combination of such signals, as may be desired, particularly for test, troubleshooting, or set up purposes as well as during an inspection run.

It will be understood that, as in FIG. 14, H and V sync lines 404, 405 interconnect (preferably continuously) the several cameras 121 (C1, C2, etc.), separator-processor unit or units 246, 247, 246R, 247R, 246L, 247L and monitor 241 in the multicamera embodiments of FIGS. 17 and 18, but are not shown in FIGS. 17 and 18 for clearer illustration of the remaining parts of such embodiments.

To insure reliable removal of defective vials by the reject unit 224 with the apparatus operating at high vial throughput rates, it is desirable that the trap door 226 (FIG. 11), to drop a defective vial, be open as long as possible without risk of also dropping or damaging preceding and succeeding nondefective vials. The maximum width of trap door opening 228 (circumferentially of the outfeed star wheel 84) is essentially the tooth pitch of the outfeed star wheel (i.e. the center-to-center spacing of circumferentially adjacent vials V in the outfeed star wheel), such that two adjacent vials V cannot simultaneously have their centers over the trap door opening 228. Thus, at a 300-vial-per-minute throughput rate, only 200 milliseconds are available for dropping a defective vial (particularly when flanked by nondefective vials which are not to be dropped) through the trap door opening 228. On the other hand, under certain circumstances such as where the blow-off nozzle 236 is not used and/or where vials of large height and diameter are being run, it may be necessary to have the trap door 226 open almost the entire 200 millisecond interval to assure reliable rejection (dropping through opening 28) of each defective vial. However, in this instance a complication arises in that actuation of the pressure fluid source P (as by opening or closing a pressure fluid valve, and forwarding and retracting the piston of pressure fluid cylinder 234) may take a substantial fraction of the available 200 millisecond interval, e.g. typically the opening sequence, from the time the source P is first signalled to open the trap door, until the trap door is fully opened, may take 40 milliseconds and the corresponding closing sequence may also take 40 milliseconds, for a total of 80 milliseconds of opening and closing lags. Thus, for high vial throughput rates at maximum rejection unit reliability, timing of trap door movements must be closely controlled and indeed controlled such that the permissible trap door open time (e.g. 200 milliseconds for a 300-vialper-minute throughput rate) is not in significant part dissipated by opening and closing lags in the trap door drive system.

Figure 11:
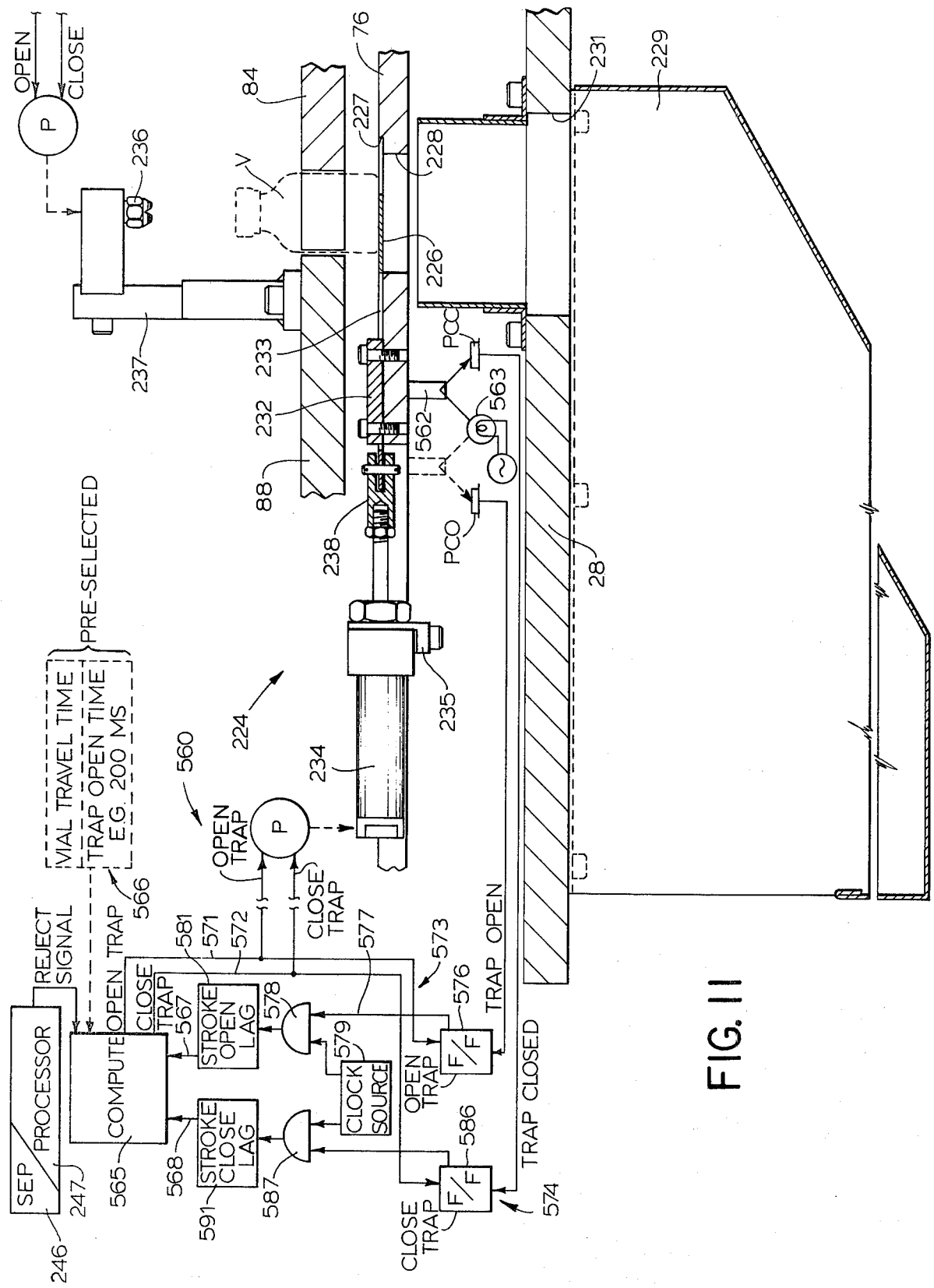
FIG. 11 is an enlarged, partially broken, sectional view substantially taken on the line XI—XI of FIG. 3.

To maximize reliability of vial removal by reject unit 224, at high vial throughput rates, the upper left portion of FIG. 11 shows a special reject trap door control 560 for the reject unit 224. The control 560 includes means for sensing the full open and full closed positions of the trap door, here including a blade 562 fixed with respect to the piston rod of trap door cylinder 234 for extension and retraction with the trap door 226. A light source 563 actuates one photocell PCO with the trap door fully opened and, on the other hand, actuates a further photocell PCC (here by reflection off the blade 562) with the trap door 226 in its fully closed position shown in FIG. 11. Light source 563 and photocells PCO and PCC are fixedly mounted with respect to the table 28 by any convenient means not shown.

Control 560 further includes a conventional computation device, preferably a microprocessor, such as the Intel 8080A, available in a complete instrument that includes its associated electronic supporting devices from Control Logic of Natick, Mass. Such computation device 565 receives a reject signal in any convenient manner from the corresponding separator processor unit 246, 247, as by insertion at the output of flip-flop 627 (where clocked well before reject unit 224 needs actuation) or the like in FIG. 15, or insertion in place of shift register 495 in FIGS. 17 or 18. The computation device 565 (FIG. 11) is preferably preprogrammed, as indicated generally by dotted lines at 566 with data corresponding to the normal vial travel time from the inspection segment of the vial orbit on vial deck 73 to the reject unit 224. The computation device 565 is similarly preprogrammed with data corresponding to the preferred trap door open time, e.g. 200 milliseconds. Also supplied to the computation device 565 are a trap opening lag time and a trap closing lag time (at 567 and 568, respectively) obtained from the last prior rejection cycle of the trap door 226. As a result of these inputs, the computation device 565 provides a trap door open signal and a trap door close signal on lines 571 and 572, respectively, which respectively initiate the opening and closing of the trap door 226, by suitable connection of the lines to the pressure source schematically indicated at P for the cylinder 234 and, if desired, for the nozzle 236 as well. It will be understood that source P may include not only a fluid pressure supply but a control valve therefor as well.

The open trap and closed trap signal lines 571 and 572, respectively, also connect to opening lag and closing lag monitoring systems 573 and 574, respectively. Opening lag monitor 573 includes a flip-flop 576 set by the open trap command signal on line 571 and reset by the trap open signal (indicating the trap 226 indeed has opened) from photocell PCO. The output line 577 of flip-flop 576 enables an AND gate 578 during the lag between the open trap signal from computation device 565 and the subsequently occurring (e.g. 40 milliseconds later) trap open signal from sensor PCO. When so enabled, AND gate 578 routes clock pulses from a source 579 to a suitable data store, such as a counter or shift register, at 581, which when AND gate 578 is thus enabled, stores clock pulses corresponding to the opening lag time (e.g. about 40 milliseconds) of the trap door 226 and in any convenient manner through mentioned lines 567 transfers this trap opening lag quantity to computing device 565.

Similarly, the trap closing lag monitor system includes a flip-flop 586 set by the close trap command signal on computing device output line 572 and reset subsequently (e.g. after about a 40 millisecond delay) by the trap closed signal from sensor PCC. Flip-flop 586 enables an AND gate 587 fed by clock source 579 for loading clock pulses into a trap closing lag store (e.g. a counter) which through mentioned line 568 supplies a quantity corresponding to the trap door closing lag time (e.g. 40 milliseconds or so) to computing device 565, such that the opening lag and closing lag counts supplied through lines 567 and 568 are usable by the computation device 565 in the next subsequent vial rejection.

As here set forth then, computation device 565 upon receiving a reject signal from the separator-processor 246, 247 as a vial then being inspected is found to be defective, thereafter times an interval equal to the vial travel time minus the trap opening lag (from line 567) and at the end of this difference time applies the open trap command signal to line 571, energizing pressure source P and setting flop-flop 576. The trap door 226 is then opened, taking a lag time which should be essentially the same as that present in counter 581 from the last rejection sequence performed. The defective vial V arrives at the opening 228 as the trap door 226 completes its opening movement and thus the vial V drops through the trap opening 228 into the reject bin 229, during the trap open time (here about 200 milliseconds) during which the star wheel 84 advances a subsequent vial to the lip of opening 228.

Since the defective vial may be followed by a nondefective vial and to avoid starting to also drop such following nondefective vial, the trap door 226 must actually start moving closed by the end of the trap open time (e.g. 200 milliseconds). To accomplish this, the computing device 565 should emit its close trap command signal on line 572 a bit (e.g. 20 milliseconds) before the end of the 200 millisecond trap open time. In this way the first part of the trap closing lag (during which air pressure is valved to and starts to build up in cylinder 234 but only the barest start of movement of trap 226 actually occurs) is out of the way as the 200 millisecond trap open time ends, after which occurs the remainder of the trap closing lag (e.g. the remaining 20 milliseconds of a 40 millisecond trap closing lag). Consequently, the trap 226 actually moves to its closed position after the 200 millisecond trap open time of the rejected vial. Thus, maximum time is alotted to dropping of the defective vial but at least some minimal part of the trap door 226 advances into the trap opening 228 just in time to prevent the following (nondefective) vial from dropping through trap opening 228.

To accomplish this, the computation device 565 can compute and time an interval starting with the open trap signal, add thereto the trap opening lag (e.g. about 40 milliseconds) from line 567 and the preselected trap open time (e.g. 200 milliseconds) and subtract therefrom a fraction (one-half or about 20 milliseconds in this example) of the stored trap closing lag on line 568 and, at the end of this computed interval, issue the trap command signal on line 572.

The closed trap condition is sensed by sensor PCC, resetting flip-flop 586 and stopping the accumulation of the trap closing lag, at store 591.

Two (or more) successive vials may be found defective. Because of the substantial distance and travel time between the inspection segment of the vial deck orbit and the reject unit 224, the reject signal for the second vial will reach the computation device 565 long before the first vial itself reaches the location of trap door 226. Accordingly, the computation device 565 will normally issue an open trap command signal for such second vial somewhat before it would otherwise issue a close trap command signal for the first vial. Accordingly, the trap door 226 simply continues open for dropping several successive defective vials. When the last of a continuous series of defective vials has substantially completed its trap open time (i.e. has dropped into the reject bin 229) the usual close trap command signal from the computation device 565 acts through the pressure source P to close the trap 226 in the usual (e.g. 40 millisecond or so) lag time.

Figure 17A:
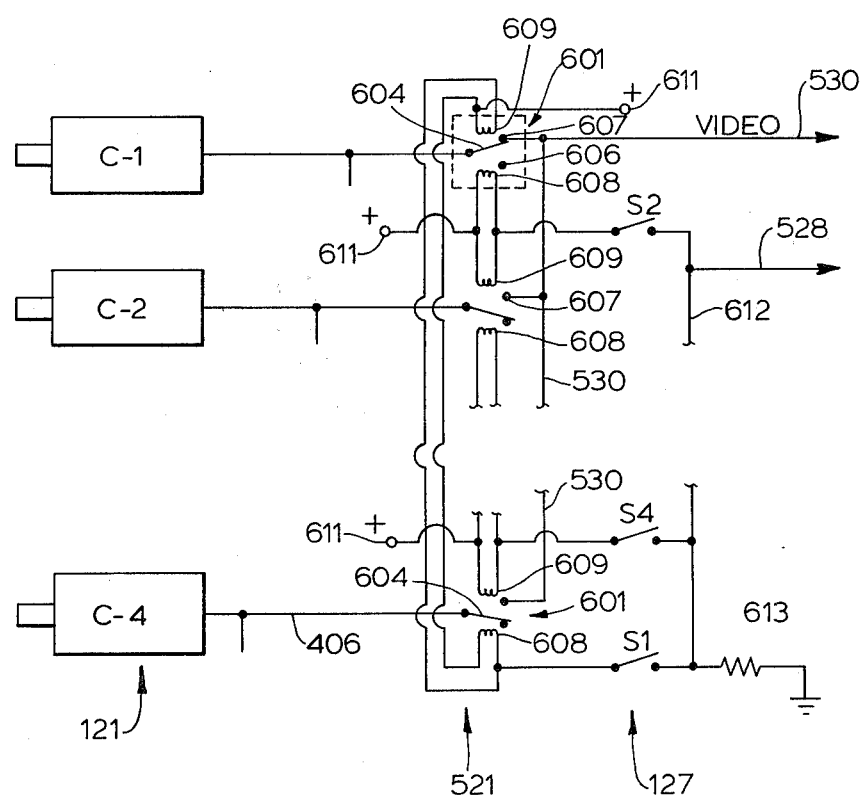

FIGS. 17 and 18, as above discussed, schematically illustrate multiple camera time sharing of a given separator-processor 246, 247 or monitor 241 by use of suitable multiplexing circuits 521 or 522. FIG. 17A shows an example of such a multiplexer circuit, here circuit 521, advantageously employing a wetted reed relay 601 for each camera. Each reed relay 601 includes a two-position switch contact 604 connected to the video output line 406 of its corresponding camera and shiftable from an off position engaging a dummy contact 606 to a transfer contact connected to the video output line 530, in common with the corresponding transfer terminals 607 of the remaining reed relays 601. Each reed relay 601 further includes a coil 608 actuable to pull the switch 604 to its dummy terminal 606 and a further coil 609 to pull the switch 604 to its transfer terminal 607. The transfer terminal selecting coil 609 of each reed relay 601 connects in parallel with the dummy terminal selecting coil 608 of the reed relay for the preceeding camera in sequence and these two parallel connected coils in turn each are connected in a series path from the positive side 611 of a voltage source, therethrough and through the camera position switch 127 for the first-mentioned camera, a common line 612, and a dropping resistor 613 to the ground side of such voltage supply.

In this embodiment, as the first of cameras 121 (Camera C-1) moves into the inspection segment of its orbit, its corresponding camera position switch 127 (i.e. the switch marked S1) closes causing the voltage source 611 to energize dummy coil 608 for the preceding camera (here camera C4) and the transfer coil 609 for mentioned camera C1. This disconnects camera C4 from video output line 530 and instead connects the video from camera C1 to video output line 530, due to switching of the switches 604 in the reed relays 601 for these two cameras. The switch S1 is only momentarily actuated and after it again opens the camera C1 remains connected to the video output line 530.

Indeed, in the embodiment shown, camera C1 remains connected to the video output line 530 until the next camera in sequence (camera C2) moves into the inspection segment of the camera orbit and its switch S2 closes momentarily, acts through relay coils 608 and 609 connected thereto, and therewith removes camera C1 video from line 530 and instead substitutes on such line the video camera C2. The cycle continues in a similar manner. Only one camera at a time is connected to output line 530 and the cameras are sequentially connected thereto by momentary actuation of their corresponding camera position switches 127.

Closure of the successively actuated switches 127, being momentary, creates a series of positive pulses on common line 612 and hence the latter line may itself be used to supply a series of camera position pulses to the line 528, rather than employing an intermediary OR gate 528' as indicated in FIGS. 17 and 18.

Although a particular preferred embodiment of the invention has been disclosed in detail for illustrative purposes, it will be recognized that variations or modifications of the disclosed apparatus, including the rearrangement of parts, lie within the scope of the present invention.

The embodiments of the invention in which an exclusive property or privilege is claimed are defined as follows:

1. An inspection system particularly for detecting excessive particulate matter in liquid filled vials or the like, comprising:
   a rotatable vial deck;
   means for infeeding vials to and outfeeding vials from corresponding vial locations on said vial deck;
   one or more inspection units each including a scanning device and a periscope means rotatable with said vial deck, a given said rotatable scanning device being axially offset from a corresponding vial location on said vial deck and aimed radially inward and along a line of sight vertically displaced from the corresponding vial position, said rotatable periscope means being oriented for bending the line of sight of said scanning device axially toward the level of said vial location and then radially outward toward said vial location, and light means for illuminating the contents of said vial.

2. The system of claim 1, in which a given said light means comprises a light source rotatable with the vial deck and aimed substantially radially inward toward the axis of rotation of said vial deck and rotatable light transfer means angled radially inward and then coaxially toward a corresponding vial location on said vial deck for endwise illumination of said vial by said radially aimed light source.

3. The system of claim 1, in which said periscope means comprises a periscope disposed radially inboard of the corresponding said scanning device and vial location on the vial deck and means mounting said periscope fixedly with respect to said vial deck as a part of the corresponding said inspection unit.

4. The system of claim 1, in which said scanning device comprises a silicon diode matrix closed circuit television camera, said system including inspection circuitry fed by said scanning devices and a color closed circuit television monitor for displaying signals derived from inspection of said vials by said scanning devices.

5. The system of claim 1, in which plural scanning devices are mounted on a scanning device deck rotatable coaxially with said vial deck and including circuitry units for processing signals from said scanning devices and fixed with respect to said scanning device deck for rotation therewith, and a slip ring unit disposed coaxially of a shell mounting said vial and scanning device decks for conveying electrical signals between fixed and rotating portions of the system.

6. The system of claim 1, in which said means for infeeding and outfeeding include an outfeed star wheel and including a reject means at the outfeed star wheel and responsive to inspection of a vial by the corresponding scanning device for discharging a defective vial from the normal orbit of said outfeed star wheel, said reject means including a reject member along a vial path actuable to an open position for rejecting a passing vial and actuable to a closed position for permitting such vial to advance therepast along the path, sensing means for sensing the open and closed positions of said reject member, computation means pre-programmable with the vial travel time from said inspection location to said reject means and with a permissible open time for said reject member, and responsive to a reject signal and to stored lag times for opening and closing said reject member for opening said reject member and holding same open for the desired time to accomplish rejection of a defective vial, while preventing premature opening or closing of said vial as would result in possible rejection of a nondefective preceding or succeeding vial.

7. The system of claim 1, wherein the scanning device at a given circumferential location is mounted on a scanning device deck and aimed radially inward toward the rotation axis of a vertical shell mounting the vial and scanning device decks, the corresponding a periscope extending axially between the vial and scanning device levels and providing a line of sight radially inward through said vial, upwardly, and then radially outward to said scanning device, said light means including a light source aimed radially inward with means angling the light path therefrom up through the bottom of the corresponding vial, so as to provide a compact machine with minimized vial deck diameter capable of continuous vial loading onto and unloading off of said vial deck despite provision of plural scanning devices and light sources.

8. The system of claim 7, in which respective circumferential arrays of said scanning devices and light sources are disposed radially out beyond corresponding vial locations on said vial deck, said light sources and scanning devices being vertically offset in opposite directions from said vial deck leaving unencumbered radially inward access to said vial deck and vials located thereon.

9. An inspection system particularly for detecting excessive particulate matter in liquid filled vials or the like, comprising:
a rotatable vial deck;
means including an infeed star wheel for infeeding vials to and an outfeed star wheel for outfeeding vials from said vial deck;
one or more inspection units rotatable with said vial deck, each said inspection unit including a scanning device axially offset from said vial deck and aimed radially inward, optical means bending the line of sight of said scanning device axially toward the plane of said vial and then radially outward toward said vial, and light means for illuminating the contents of said vial; said vial deck including a vial supporting puck mounted for spinning with respect to said vial deck and means for holding a said vial coaxially on said puck in the vial deck orbit from the infeed star wheel to the outfeed star wheel, said puck and vial holding means comprising parts of a given said inspection unit, spinning means engageable with said puck to spin same during one segment of the clamped vial orbit, said vial stopping its spinning with respect to said vial deck in a next segment of such clamped vial orbit, means coordinated with said vial advancement into an inspection segment of said clamped vial orbit to obtain video signals from the scanning device viewing the vial, for inspection purposes.

10. The system of claim 9, in which said coordinate means include a reed switch mounted for rotation with each said inspection unit and a magnet fixed at a point along the orbit of said inspection unit for triggering successively presented reed switches so as to synchronize inspection video flow from the corresponding scanning devices with entry of each such scanning device into said inspection segment of the vial deck orbit.

11. An inspection system for detecting excessive particle content in liquid filled vials or the like, comprising:
scanning means for line scanning a field superposed on an illuminated, fluid containing vial to detect suspended particles therein;
means coupled to said scanning means and responsive to scanning of such a particle thereby for producing a corresponding pulse signal;
a processer circuit including detector circuit means for detecting the presence of such a pulse signal at each of several adjacent points on the same scan line of said scanning device and then in each of several adjacent scan lines of a field of said scanning device, and then in each of several successive fields of scan of said scanning device;
means coupled to said processer circuit and responsive to such a detecting for indicating that such vial has an unacceptable particle content.

12. The system of claim 11 in which said means coupled to said processing circuit and responsive to a detection includes a reject means for rejecting a vial detected to have an unacceptable particle content, said system including means for moving vials successively past a first location for inspection by a said scanning means and then past said reject means, and means delaying actuation of said reject means for a time sufficient to permit the unacceptable vial to travel from said inspection location to said reject means.

13. The system of claim 11 in which each said scanning means comprises a closed circuit television camera, said system including means for fixedly locating a vial with respect to and in the line of sight of said camera, said camera including means for sensing when the focus of the camera is finer than that necessary to detect the minimum sized particle being sought.

14. The system of claim 11 including means for moving said vial along a path past a first location for inspection by said scanning means, a reject means spaced downstream along said path from said inspection location, said processor circuit providing a reject signal upon said detection of said pulse signal in said several successive scanning fields for indicating a vial to be rejected, said reject means including a reject member along the vial path actuable to an open position for rejecting a passing vial and actuable to a closed position for permitting such vial to advance therepast along the path;
sensing means for sensing the open and closed positions of said reject member, computation means pre-programmable with the vial travel time from said inspection location to said reject means and with a permissible open time for said reject member, and responsive to a reject signal and to stored lag times for opening and closing said reject member for opening said reject member and holding same open for the desired time to accomplish rejection of a defective vial, while preventing premature opening or closing of said vial as would result in possible rejection of a nondefective preceding or succeeding vial.

15. The system of claim 11 in which said scanning means is a low persistence black and white closed circuit television camera.

16. The system of claim 15 in which said camera is a silicon diode matrix camera.

17. The system of claim 11 in which said processor circuit further includes a window circuit means for generating a window signal during those times when said scanning device is scanning a window area located within the scanning field of said scanning device and spaced inboard from the edges of said scanning field, said window circuit means being connected to said detecting circuit means for enabling said detecting circuit means only during scanning within said window area, said window area being adapted to overlie part of said vial scanned by said scanning means.

18. The system of claim 17 including a color closed circuit television monitor having a display screen energizable in a first color and a scanning beam synchronized with said scanning device, said monitor being connected to said window circuit for displaying said window in a second color on said display screen, said monitor being further connected to said detection circuit means for displaying a visible indicator in a third color on said screen in response to detection of a said pulse signal at least at said adjacent points in one scan line.

19. The system of claim 17 in which said scanning means comprises a closed circuit television camera, said window circuit including means responsive to coincidence of said window signal and a said pulse signal, indicating crossing of a possible particle in said vial by the scanning beam of said camera, for producing an inspection window signal, said detecting circuit means including a horizontal sizer circuit and clock means connected thereto, said horizontal sizer circuit including means responsive to coincidence of an inspection window signal and a series of clock pulses from said clock means corresponding to a preselected fraction of the width of the horizontal scan line of said camera for producing a horizontal size pulse, said detecting circuit means further including a vertical sizer circuit connected to said horizontal sizer circuit, said vertical sizer circuit including means for storing a horizontal size pulse for the remainder of the horizontal scan line in which said horizontal size pulse occurs and means synchronized with the occurence of successive horizontal scan lines through said window area and responsive to storage of horizontal size pulses for a preselected number of successive horizontal scan lines for producing a horizontal-vertical size pulse, said detecting circuit means further including a frame counter circuit connected to said vertical sizer circuit and including further storage means for storing said horizontal-vertical size pulses, said frame counter circuit being synchronized with occurrence of successive scanning fields of said camera and responsive to occurrence of a horizontal-vertical size signal in a preselected number of successive fields of said camera for actuating said indicating means.

20. The system of claim 19 in which said window signal comprises two components, namely a horizontal window signal and a vertical window signal, which respectively define a portion of each horizontal scan line crossing the window area and define the group of successive scan lines crossing the window area, said window circuit means including gate means responsive to concurrence of at least said horizontal window signal, vertical window signal, and pulse signal for producing said inspection window signal.

21. The system of claim 11 in which said scanning means comprises a series of closed circuit television cameras mounted for movement along a path, a vial support means for each said camera and being movable therewith along said path for supporting a corresponding vial for inspection by the corresponding camera, a fixed inspection location on said path such that each camera is to inspect its corresponding vial as it passes through said inspection location on said path, camera location responsive means providing a camera position signal when each camera in succession enters said inspection location along said path.

22. The system of claim 21 including rotatable deck means supporting said cameras and their corresponding vial support means for rotation through an orbit, said orbit being said path, said camera location responsive means comprising a plurality of reed switches in one-to-one relation with said cameras, said cameras and switches being correspondingly circumferentially distributed on said deck means for rotation therewith, said camera location responsive means further including a fixed magnet means adjacent said rotating deck means and rotating reed switches for sequentially actuating said reed switches as they rotate therepast and causing said reed switches to provide said camera position signals as their corresponding cameras reach said inspection location along the camera orbit.

23. The system of claim 21 including camera multiplex means responsive to sequential actuation of said camera location responsive means for switching the video output of successive cameras entering said inspection location to said means coupled to said scanning means and therethrough to said processer circuit, the means responsive to detection including a reject mechanism actuable to reject a vial having excessive particle content and shift register means coupling said processor circuit to said reject mechanism, said shift register having a clock input connected to said camera location responsive means and itself responsive to a preselected number of said camera position signals for advancing said shift register, said reject mechanism being spaced downstream along said path from said inspection location, such that said shift register delays actuation of said reject mechanism sufficiently to permit the travel of the offending vial from said inspection location to said reject mechanism, said system further including a video display monitor and a monitor multiplex means interposed between the video outputs of said plurality of cameras and said monitor, said monitor multiplex means being responsive to movement of successive cameras past said inspection location for displaying, in succession, the outputs thereof on said monitor.

24. The system of claim 23 in which said first mentioned camera multiplex means has connected thereto the video outputs of only alternate ones of said cameras and only the corresponding, alternate ones of said camera location responsive means so as to apply the video output of said alternate cameras, in sequence, to said first mentioned means coupled to said scaning means and therethrough to said first mentioned processor circuit, a second camera multiplex means having connected thereto the video outputs of the remaining ones of said cameras in sequence and being connected to the corresponding remaining ones of said camera location responsive means for providing at its output the video from said remaining cameras in sequence as such cameras traverse said inspection location, a second means coupled to said scanning means in parallel to said first mentioned means coupled to said scanning means and a second processer circuit fed by said second means coupled to said scanning means, the outputs of said first mentioned and second processor circuits being coupled by OR gate means to said shift register, such that said cameras time share two said processer circuits and a single video monitor.

25. The system of claim 23 in which said multiplex means includes a plurality of reed relays, one for each camera, connected to the said multiplex means, wherein said reed delays are sequentially actuable to sequentially switch the video outputs of the said cameras connected to the input side of said multiplex means, to a common output of said multiplex means.

26. The system of claim 25 in which each said reed relay has first and second coils respectively actuable for switching a contact of such reed relay between the video output of said one multiplex means and an inactive contact, such that actuation of said first coil of a given reed relay switches the corresponding camera video to the video output of said one multiplex means and activation of the second coil of such reed relay switches the video output for that camera to said inactive contact, the first coil of each reed relay being connected in parallel with the second coil of the reed relay associated with the next camera in succession in said series of cameras, said camera location responsive means comprising a reed switch for each camera actuable when the video from such camera is to be inspected, each said reed switch being connected in series with a voltage source and the parallel connected reed relay coils of its associated camera and the camera preceding the latter, such that actuation of said reed switch disconnects said preceding camera from said one multiplex means output line and instead connects thereto the camera corresponding to the actuated camera location switch.

27. An inspection system for detecting excessive particulate matter in liquid filled vials or the like, comprising:
 a television camera for scanning a fluid containing vial and producing a video signal output variable as the camera scanning beam crosses particles in the vial and other discontinuities in the scene viewed thereby;
 means responsive to said video signal output from said television camera for producing pulses at least when the camera scanning beam sweeps over particles in said vial;
 detector circuit means responsive to a particular pattern of occurrence of said pulses, as would correspond to scanning of a particle large enough to merit rejection of the vial for producing a vial reject signal;
 focus sensing means for receiving said video signal and including means responsive to a video signal pulse as would be generated by scanning of a particle or the like somewhat narrower than detected by said detector circuit means, said focus sensing means including means responsive to absence of such a video signal pulse during the period of scanning of the vial by said television camera for producing a further reject pulse, wherein said further reject pulse suggests that said camera is not properly focused;
 reject means operatively connected to said detector circuit means and focus sensing means and responsive to a reject signal from either for indicating that the vial is to be rejected.

28. The system of claim 27 in which said focus sensing means includes, as said means responsive to a video signal pulse, a shift register having a data input and means responsive to conditions corresponding to scanning of a vial for applying the camera video to such data input, such shift register further having a shift input for receiving clock pulses at a frequency substantially higher than the horizontal scanning frequency of said camera for shifting samples of said video signal serially through said shift register for a given camera scan line, said shift register further having a plurality of parallel outputs including central and flanking outputs, said central outputs being polarity inverted with respect to said flanking outputs, and including an AND-function gate means having parallel inputs receiving said inverted and noninverted outputs of said shift register and responsive to a video signal pulse of sufficient duration as to trigger said central outputs but not said flanking outputs of such shift register for triggering said AND-function gate to produce an in-focus signal, said detector circuit means including a similar shift register having outputs similar in number to said first mentioned shift register and being of common polarity with respect to each other, but the detector circuit means further including a further AND-function gate having parallel inputs connected to the parallel outputs of said further shift register, said further shift register having pulses from said pulse producing means shifted therethrough serially substantially at the rate of said clock pulses such that said further AND-function gate is triggered by said further shift register only in response to scanning a particle wider than required to trigger said first mentioned AND-function gate, wherein triggering of said first mentioned AND-function gate suggests that the camera is in sufficient focus to detect particles of even the smallest size of interest.

29. The system of claim 28 including flip-flop means switched to an in focus memory condition by triggering of said first mentioned AND-function gate, and means responsive to inspection of a given vial for at least a portion of an inspection period and further responsive to absence of an in focus state in said flip-flop for producing a said further reject signal.

30. An inspection system particularly for detecting excessive particulate matter in liquid filled vials or the like, comprising:
 a rotatable vial deck;
 means for infeeding vials to and outfeeding vials from said vial deck, said infeed and outfeed means each comprising a rotatable star wheel, said star wheels and rotatable vial deck lying close adjacent each other with their axes substantially parallel, said vial deck and star wheels each having the same number of circumferentially spaced vial locations, such that blocking of a given infeed star wheel vial location to prevent entry of a vial thereinto positively prevents placement of vials by the infeed star wheel on the corresponding vial location of the rotatable vial deck, such that the system can be run through a number of vial deck orbits with selected vial locations on the vial deck left unoccupied but with the remaining vial locations on the vial deck each provided with a vial;

one or more inspection units rotatable with said vial deck, each said inspection unit including a scanning device axially offset from said vial deck and aimed radially inward, optical means bending the line of sight of said scanning device axially toward the plane of said vial and then radially outward toward said vial, and light means for illuminating the contents of said vial.

31. An inspection system particularly for detecting excessive particulate matter in liquid filled vials or the like, comprising:

a rotatable vial deck;

means for infeeding vials to and outfeeding vials from corresponding vial locations on said vial deck;

one or more inspection units each including a scanning device and a periscope means rotatable with said vial deck, a given said rotatable scanning device being axially offset from a corresponding vial location on said vial deck and aimed radially inward therebeyond, said rotatable periscope means being oriented for bending the line of sight of said scanning device axially toward the level of said vial location and then radially outward toward said vial location, and light means for illuminating the contents of said vial;

a frame with respect to which said vial deck is rotatable, a semicircular cam fixed with respect to said frame and loosely coaxially surrounding said periscope means axially between said scanning device and vial deck, each said inspection unit including a chuck vertically slidably mounted above a corresponding vial location on said vial deck and lowerable into gripping engagement with the top of a vial at such location, a substantially horizontal lever mounted for rotation with and vertically pivotable with respect to said vial deck, said lever vertically supporting said chuck and riding said cam to lift the chuck above the level of said vials for loading and unloading of vials with respect to said vial deck and to allow said chuck to ride on said vials during orbiting of the latter with said vial deck.

32. An inspection system for detecting excessive particle content in liquid filled vials or the like, comprising:

a black and white television camera located for line scanning a field superposed on a fluid containing vial to detect suspended particles therein;

a color television monitor having a display screen, said camera and monitor having scanning beams which are synchronized;

particle detection circuit means responsive to the video output of said camera for displaying spots on said monitor screen in response to scanning by the camera of the particles in said vial, said detection circuit means including size detection means responsive to signals derived from said camera video for displaying a visible warning pattern on said monitor screen upon scanning by the camera of a particle of substantial size and at least one of said displays being of preselected color;

window circuit means synchronized with the scanning beams of said camera and monitor and connected with said detection circuit means for limiting operation of the latter to a central portion of the field of view of said camera and monitor, said window circuit means being connected to said monitor for display of said window area and the screen area bounding such window area in colors contrasting with each other and with at least one of said spot and warning image.

33. An inspection system particularly for detecting excessive particulate matter in liquid filled vials or the like, comprising:

a rotatable vial deck having circumferentially distributed vial locations thereon;

means for infeeding vials to and outfeeding vials from said vial deck;

a scanning device rotatable with said vial deck and having a line of sight axially offset from a corresponding vial location on said deck;

a periscope means rotatable with said vial deck in continuously fixed opposed relation to a corresponding vial location on said vial deck, said periscope means having its one end radially opposing said scanning device and its other end radially opposing said corresponding vial location; and light means for illuminating the contents of said vial.

* * * * *

UNITED STATES PATENT OFFICE
CERTIFICATE OF CORRECTION

Patent No. 4,172,524          Dated October 30, 1979

Inventor(s) James P. Holm, Joe W. Clapper, Ronald J. Dudley and Chester C. Sperry It is certified that error appears in the above-identified patent and that said Letters Patent are hereby corrected as shown below:

Column 1, line 49; change "shck" to ---shock---.

Column 4, line 4; change "rotatable" to ---rotatably---.

Column 5, line 39; change "bial" to ---vial---.

Column 12, line 53; change "116" to ---161---.

Column 16, line 29; change "oneshots" to ---one-shots---.

Column 31, line 18; after "corresponding" delete "a".

Column 31, line 67; change "coordinate" to ---coordinated---.

Column 35, line 13; change "delays" to ---relays---.

Signed and Sealed this

First Day of April 1980

[SEAL]

Attest:

SIDNEY A. DIAMOND

Attesting Officer      Commissioner of Patents and Trademarks